(12) United States Patent
Lam et al.

(10) Patent No.: US 7,994,390 B2
(45) Date of Patent: Aug. 9, 2011

(54) USE OF GMRD22-LIKE GENES TO PROTECT AGAINST ABIOTIC STRESS

(75) Inventors: Hon-Ming Lam, Hong Kong (CN); Samuel Sai Ming Sun, Hong Kong (CN); Gui Hua Shao, Beijing (CN)

(73) Assignee: The Chinese University of Hong Kong, Hong Kong (CN)

( * ) Notice: Subject to any disclaimer, the term of this patent is extended or adjusted under 35 U.S.C. 154(b) by 124 days.

(21) Appl. No.: 11/904,906

(22) Filed: Sep. 28, 2007

(65) Prior Publication Data

US 2008/0184385 A1 Jul. 31, 2008

Related U.S. Application Data

(60) Provisional application No. 60/848,113, filed on Sep. 29, 2006.

(51) Int. Cl.
*C12N 15/82* (2006.01)
(52) U.S. Cl. .................................. 800/278; 435/468
(58) Field of Classification Search .................. None
See application file for complete search history.

(56) References Cited

U.S. PATENT DOCUMENTS

| | | | |
|---|---|---|---|
| 5,380,831 A | 1/1995 | Adang et al. | |
| 5,436,391 A | 7/1995 | Fujimoto et al. | |
| 2004/0009476 A9 | 1/2004 | Harper et al. | |
| 2004/0031072 A1* | 2/2004 | La Rosa et al. | 800/278 |
| 2008/0148432 A1* | 6/2008 | Abad | 800/279 |

OTHER PUBLICATIONS

Wells (Biochemistry 29:8509-8517, 1990).*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Granger et al. (Genome, 45:693-701, 2002).*
Ngo et al., (The Protein Folding Problem and Tertiary Structure Prediction, K. Merz., and S. Le Grand (eds.) pp. 492-495,1994).*
GenBank Accession No. NM_122472, (May 2008).
GenBank Accession No. AY634282, (Aug. 2008).
GenBank Accession No. AF319165, (Nov. 2001).
Callahan et al., J. Am. Soc. Hortic. Sci. (1993) 118:531-537.
Hanana et al., C. R. Biol. (2008) 331:569-578.
Cheung et al., J. of Experimental Botany (2007) 58(15/16):4147-4159.
Abe et al., Plant Cell (1997) 9:1859-1868.
Ashraf, Crit. Rev. Plant Sci. (1994) 13:17-42.
Bechtold and Pelletier, in Martinez-Zapater and Salinas (Eds.), *Arabidopsis* Protocols, Humana Press Inc., Totowa, 1993, pp. 259-266.
Brears et al., Plant Physiol. (1993) 103:1285-1290.
Finckh et al., Biotechniques (1991) 10:35-38.
Hoagland and Arnon, Calif. Agric. Expt. Circ. (1938) 347:1-39.
Jackson and Larkins, Plant Physiol. (1976) 57:5-10.
Jain and Selvaraj, Biotechnology Annual Review (1997) 3:245-267.
Kumar et al., Bioinformatics (2001) 17:1244-1245.
Maas and Hoffman, J. Irrig. Drain. Eng. (1977) 103:115-134.
Meinkoth and Wahl, Anal. Biochem. (1984) 138:267-284.
Sambrook and Russell (eds.) 2001. Amplification of cDNA generated by reverse transcription of mRNA (RT-PCR). In: *Molecular Cloning—A Laboratory Manual* (3rd ed.), Chapter 8, pp. 8.46-8.53.
Thompson et al., Nucleic Acids Res. (1994) 22:4673-4680.
Xiong et al., Plant Cell (2001) 13:2063-2083.
Yamaguchi-Shinozaki and Shinozaki, Mol. Gen. Genet. (1993) 238:17-25.
Zhang and Luo, Journal of Xinjiang Agricultural University (2005) 28(2):22-24, Abstract only.
Office Action from Chinese Patent Application No. 200780035881.9, mailed on Jun. 7, 2010, 9 pages.

* cited by examiner

*Primary Examiner* — Vinod Kumar
(74) *Attorney, Agent, or Firm* — Morrison & Foerster LLP

(57) ABSTRACT

Provided herein are the protein and nucleic acid sequences of GmRD22. Further provided herein are methods for conferring abiotic stress tolerance to a plant cell or plant by introducing and expressing an isolated polynucleotide encoding a GmRD22 protein in the cells of the plant. Transgenic plants transformed with an isolated polynucleotide encoding a GmRD22 protein, as well as seeds and progeny derived from these plants, are also provided.

8 Claims, 14 Drawing Sheets

Wild type and transgenic rice in the open field before treatment

Wild type and transgenic rice being treated with sea water (equivalent to 2% salt) for 1 month (a) Drought (b) 200mM NaCl

SEQUENCE LISTING

```
<160> NUMBER OF SEQ ID NOS: 17

<210> SEQ ID NO 1
<211> LENGTH: 1032
<212> TYPE: DNA
<213> ORGANISM: Artificial Sequence
<220> FEATURE:
<223> OTHER INFORMATION: GmRD22

<400> SEQUENCE: 1
atggagtatc gtctcctacc cattttact  ttactcaatc ttgcactggt ggcaatccat      60
gctgctttac ctcctgaagt ttactggaag tcggtgcttc ctactacgcc aatgccaaaa     120
gccatcactg atatccttta ccccgattgg gtggaagaga aaagtacctc agtgaatgtt     180
ggaggcaagg gcgtaaacgt gcatgcagga aaaggaggag gtggcaccaa tgtcaacgtt     240
ggtggaaaag gatcaggcgg aggcgtgaac gtgcatgcag gtcacaaggg aaagccagtg     300
catgtttctg ttggctcaaa gtctccattc aattacatct acgcttcaac ggagactcaa     360
ttacacgatg accccaacgt cgcactcttc ttcttggaaa aggacttgca tcccggaaca     420
aagttgaact tgcacttcac caccagttcc aatattcaag ccacattctt gccacgccaa     480
```

```
gttgcggatt ctataccctt ttcatccagc aaggtggagg ttgtattcaa caagttttcc      540
gtaaaacccg ggtcagagga ggcccagatc atgaagaata ctctcagtga gtgtgaagag      600
ggtggcatca aaggagagga aaagtactgt gccacttcgc ttgaatccat gattgatttc      660
agcacttcca agcttggaaa aaatgttgag gttgtgtcca cggaagtagt ggaggacaag      720
gaaacgggat tgcagaaata caccgtagca ccgggagtga acaagttatc agggacaag       780 gctgttgtgt gccacaagca aactaccct tatgctgttt tttactgtca caaactgag        840 accacaagag cttactctgt gcctttggag ggtgctaatg gggttagggt taaagcggta      900
gcagtgtgcc acactcacac gtcggaatgg aaccctaaac atttggcctt tcaagtgctc      960
aaagttaagc caggaaccgt tcctgtctgc cacttcctac ctgaggatca tgttgtttgg     1020
gttcccaagt ag                                                         1032
```

<210> SEQ ID NO 2
<211> LENGTH: 343
<212> TYPE: PRT
<213> ORGANISM: Artificial Sequence
<220> FEATURE:
<223> OTHER INFORMATION: GmRD22

<400> SEQUENCE: 2

```
Met Glu Tyr Arg Leu Leu Pro Ile Phe Thr Leu Leu Asn Leu Ala Leu
 1               5                  10                  15

Val Ala Ile His Ala Ala Leu Pro Pro Glu Val Tyr Trp Lys Ser Val
            20                  25                  30

Leu Pro Thr Thr Pro Met Pro Lys Ala Ile Thr Asp Ile Leu Tyr Pro
        35                  40                  45

Asp Trp Val Glu Glu Lys Ser Thr Ser Val Asn Val Gly Gly Lys Gly
    50                  55                  60

Val Asn Val His Ala Gly Lys Gly Gly Gly Thr Asn Val Asn Val
65                  70                  75                  80

Gly Gly Lys Gly Ser Gly Gly Gly Val Asn Val His Ala Gly His Lys
                85                  90                  95

Gly Lys Pro Val His Val Ser Val Gly Ser Lys Ser Pro Phe Asn Tyr
            100                 105                 110

Ile Tyr Ala Ser Thr Glu Thr Gln Leu His Asp Asp Pro Asn Val Ala
        115                 120                 125

Leu Phe Phe Leu Glu Lys Asp Leu His Pro Gly Thr Lys Leu Asn Leu
    130                 135                 140

His Phe Thr Thr Ser Ser Asn Ile Gln Ala Thr Phe Leu Pro Arg Gln
145                 150                 155                 160

Val Ala Asp Ser Ile Pro Phe Ser Ser Lys Val Glu Val Phe
                165                 170                 175

Asn Lys Phe Ser Val Lys Pro Gly Ser Glu Glu Ala Gln Ile Met Lys
            180                 185                 190

Asn Thr Leu Ser Glu Cys Glu Glu Gly Gly Ile Lys Gly Glu Glu Lys
        195                 200                 205

Tyr Cys Ala Thr Ser Leu Glu Ser Met Ile Asp Phe Ser Thr Ser Lys
    210                 215                 220

Leu Gly Lys Asn Val Glu Val Ser Thr Glu Val Val Glu Asp Lys
225                 230                 235                 240

Glu Thr Gly Leu Gln Lys Tyr Thr Val Ala Pro Gly Val Asn Lys Leu
                245                 250                 255

Ser Gly Asp Lys Ala Val Val Cys His Lys Gln Asn Tyr Pro Tyr Ala
```

```
                    260                 265                 270
Val Phe Tyr Cys His Lys Thr Glu Thr Thr Arg Ala Tyr Ser Val Pro
            275                 280                 285

Leu Glu Gly Ala Asn Gly Val Arg Val Lys Ala Val Ala Val Cys His
        290                 295                 300

Thr His Thr Ser Glu Trp Asn Pro Lys His Leu Ala Phe Gln Val Leu
305                 310                 315                 320

Lys Val Lys Pro Gly Thr Val Pro Val Cys His Phe Leu Pro Glu Asp
                325                 330                 335

His Val Val Trp Val Pro Lys
            340

<210> SEQ ID NO 3
<211> LENGTH: 392
<212> TYPE: PRT
<213> ORGANISM: Arabidopsis thaliana

<400> SEQUENCE: 3

Met Ala Ile Arg Leu Pro Leu Ile Cys Leu Leu Gly Ser Phe Met Val
1               5                   10                  15

Val Ala Ile Ala Ala Asp Leu Thr Pro Glu Arg Tyr Trp Ser Thr Ala
            20                  25                  30

Leu Pro Asn Thr Pro Ile Pro Asn Ser Leu His Asn Leu Leu Thr Phe
        35                  40                  45

Asp Phe Thr Asp Glu Lys Ser Thr Asn Val Gln Val Gly Lys Gly Gly
    50                  55                  60

Val Asn Val Asn Thr His Lys Gly Lys Thr Gly Ser Gly Thr Ala Val
65                  70                  75                  80

Asn Val Gly Lys Gly Gly Val Arg Val Asp Thr Gly Lys Gly Lys Pro
                85                  90                  95

Gly Gly Gly Thr His Val Ser Val Gly Ser Gly Lys Gly His Gly Gly
            100                 105                 110

Gly Val Ala Val His Thr Gly Lys Pro Gly Lys Arg Thr Asp Val Gly
        115                 120                 125

Val Gly Lys Gly Gly Val Thr Val His Thr Arg His Lys Gly Arg Pro
    130                 135                 140

Ile Tyr Val Gly Val Lys Pro Gly Ala Asn Pro Phe Val Tyr Asn Tyr
145                 150                 155                 160

Ala Ala Lys Glu Thr Gln Leu His Asp Asp Pro Asn Ala Ala Leu Phe
                165                 170                 175

Phe Leu Glu Lys Asp Leu Val Arg Gly Lys Glu Met Asn Val Arg Phe
            180                 185                 190

Asn Ala Glu Asp Gly Tyr Gly Gly Lys Thr Ala Phe Leu Pro Arg Gly
        195                 200                 205

Glu Ala Glu Thr Val Pro Phe Gly Ser Glu Lys Phe Ser Glu Thr Leu
    210                 215                 220

Lys Arg Phe Ser Val Glu Ala Gly Ser Glu Glu Ala Glu Met Met Lys
225                 230                 235                 240

Lys Thr Ile Glu Glu Cys Glu Ala Arg Lys Val Ser Gly Glu Glu Lys
                245                 250                 255

Tyr Cys Ala Thr Ser Leu Glu Ser Met Val Asp Phe Ser Val Ser Lys
            260                 265                 270

Leu Gly Lys Tyr His Val Arg Ala Val Ser Thr Glu Val Ala Lys Lys
        275                 280                 285

Asn Ala Pro Met Gln Lys Tyr Lys Ile Ala Ala Ala Gly Val Lys Lys
```

```
              290                 295                 300
Leu Ser Asp Asp Lys Ser Val Val Cys His Lys Gln Lys Tyr Pro Phe
305                 310                 315                 320

Ala Val Phe Tyr Cys His Lys Ala Met Met Thr Thr Val Tyr Ala Val
                325                 330                 335

Pro Leu Glu Gly Glu Asn Gly Met Arg Ala Lys Ala Val Ala Val Cys
                340                 345                 350

His Lys Asn Thr Ser Ala Trp Asn Pro Asn His Leu Ala Phe Lys Val
                355                 360                 365

Leu Lys Val Lys Pro Gly Thr Val Pro Val Cys His Phe Leu Pro Glu
                370                 375                 380

Thr His Val Val Trp Phe Ser Tyr
385                 390

<210> SEQ ID NO 4
<211> LENGTH: 387
<212> TYPE: PRT
<213> ORGANISM: Brassica napus

<400> SEQUENCE: 4

Met Ala Ile Arg Leu Ser Leu Ile Cys Leu Leu Val Ser Val Thr Ala
  1               5                  10                  15

Ile Ala Ala Asp Leu Thr Pro Glu Arg Tyr Trp Asn Ser Ala Leu Pro
                 20                  25                  30

Asn Thr Pro Ile Pro Asn Ser Leu Arg His Leu Phe Thr Ser Asp Phe
             35                  40                  45

Ser Asp Glu Glu Ser Thr Asn Val Gln Val Gly Lys Gly Gly Val Asn
         50                  55                  60

Val Tyr Thr Gly Lys Gly Lys Pro Gly Gly Thr Ala Val Asn Val
 65                  70                  75                  80

Gly Lys Gly Gly Val His Val Asn Thr Gly Lys Gly Lys Gly Thr His
                 85                  90                  95

Val Ser Val Ser Gly Gly Lys Gly His Gly Gly Val Gly Val His
             100                 105                 110

Thr Gly Lys Pro Gly Lys Arg Thr Asp Val Gly Val Gly Lys Gly Gly
         115                 120                 125

Val Ile Val His Thr Arg His Lys Gly Lys Pro Val Tyr Val Gly Val
     130                 135                 140

Lys Pro Gly His Asn Pro Phe Ala Tyr Asn Tyr Ala Ala Ser Glu Thr
145                 150                 155                 160

Gln Leu His Asp Asp Pro Lys Ala Ala Leu Phe Leu Glu Lys Asp
                 165                 170                 175

Met Val Pro Gly Lys Ala Met Asn Leu Arg Phe Asn Ala Glu Asp Gly
                 180                 185                 190

Tyr Asn Gly Lys Thr Ala Phe Leu Pro Arg Gly Glu Ala Glu Thr Val
             195                 200                 205

Pro Phe Gly Ser Glu Lys Ser Ser Glu Ile Leu Asn Thr Phe Ser Val
         210                 215                 220

Lys Pro Gly Ser Gly Glu Ala Glu Met Met Lys Lys Thr Ile Glu Glu
225                 230                 235                 240

Cys Glu Ala Lys Arg Val Gly Gly Glu Lys Tyr Cys Ala Thr Ser
                 245                 250                 255

Leu Glu Ser Met Val Asp Phe Ser Val Ser Lys Leu Gly Lys Asp His
             260                 265                 270

Val Arg Ala Val Ser Thr Glu Val Ala Glu Lys Asn Ala Pro Met Gln
```

-continued

```
                275                 280                 285
Lys Tyr Arg Ile Ala Ala Gly Val Lys Leu Ser Asp Asp Lys
            290                 295                 300
Ser Val Val Cys His Lys Gln Lys Tyr Pro Phe Ala Val Phe Tyr Cys
305                 310                 315                 320
His Lys Ala Met Met Thr Ser Val Tyr Ala Val Pro Leu Glu Gly Glu
                    325                 330                 335
Asn Gly Leu Arg Ala Lys Ala Val Ala Val Cys His Lys Asn Thr Ser
                340                 345                 350
Ala Trp Asn Pro Asn His Leu Ala Phe Lys Val Leu Lys Val Lys Pro
            355                 360                 365
Gly Ser Val Pro Val Cys His Phe Leu Pro Glu Thr His Val Val Trp
            370                 375                 380
Phe Ser Tyr
385

<210> SEQ ID NO 5
<211> LENGTH: 305
<212> TYPE: PRT
<213> ORGANISM: Glycine max

<400> SEQUENCE: 5

Met Glu Phe His Cys Leu Pro Ile Phe Leu Tyr Leu Asn Leu Met Leu
1               5                   10                  15
Met Thr Ala Asn Ala Ala Leu Thr Pro Arg His Tyr Trp Glu Thr Met
            20                  25                  30
Leu Pro Arg Thr Pro Leu Pro Lys Ala Ile Thr Glu Leu Leu Ser Leu
        35                  40                  45
Glu Ser Arg Ser Ile Phe Glu Tyr Ala Gly Asn Asp Asp Gln Ser Glu
    50                  55                  60
Ser Arg Ser Ile Leu Gly Tyr Ala Gly Tyr Asn Gln Asp Glu Asp Asp
65                  70                  75                  80
Val Ser Lys His Asn Ile Gln Ile Phe Asn Arg Leu Phe Phe Leu Glu
                85                  90                  95
Glu Asp Leu Arg Ala Gly Lys Ile Phe Asn Met Lys Phe Val Asn Asn
            100                 105                 110
Thr Lys Ala Thr Val Pro Leu Leu Pro Arg Gln Ile Ser Lys Gln Ile
        115                 120                 125
Pro Phe Ser Glu Asp Lys Lys Lys Gln Val Leu Ala Met Leu Gly Val
    130                 135                 140
Glu Ala Asn Ser Ser Asn Ala Lys Ile Ile Ala Glu Thr Ile Gly Leu
145                 150                 155                 160
Cys Gln Glu Pro Ala Thr Glu Gly Glu Arg Lys His Cys Ala Thr Ser
                165                 170                 175
Leu Glu Ser Met Val Asp Phe Val Ser Ala Leu Gly Lys Asn Val
            180                 185                 190
Gly Ala Phe Ser Thr Glu Lys Glu Arg Glu Thr Glu Ser Gly Lys Phe
        195                 200                 205
Val Val Val Lys Asn Gly Val Arg Lys Leu Gly Asp Asp Lys Val Ile
    210                 215                 220
Ala Cys His Pro Met Ser Tyr Pro Tyr Val Val Phe Gly Cys His Leu
225                 230                 235                 240
Val Pro Arg Ser Ser Gly Tyr Leu Val Arg Leu Lys Gly Glu Asp Gly
                245                 250                 255
Val Arg Val Lys Ala Val Val Ala Cys His Arg Asp Thr Ser Lys Trp
```

```
                    260                 265                 270
Asp His Asn His Gly Ala Phe Lys Val Leu Asn Leu Lys Pro Gly Asn
            275                 280                 285
Gly Thr Val Cys His Val Phe Thr Glu Gly Asn Leu Leu Trp Leu Pro
            290                 295                 300
Asn
305

<210> SEQ ID NO 6
<211> LENGTH: 630
<212> TYPE: PRT
<213> ORGANISM: Lycopersicon esculentum

<400> SEQUENCE: 6

Met His Thr Lys Ile His Leu Pro Pro Cys Ile Leu Leu Leu Leu Leu
 1               5                  10                  15
Phe Ser Leu Pro Ser Phe Asn Val Val Gly Gly Asp Gly Glu Ser
            20                  25                  30
Gly Asn Pro Phe Thr Pro Lys Gly Tyr Leu Ile Arg Tyr Trp Lys Lys
            35                  40                  45
Gln Ile Ser Asn Asp Leu Pro Lys Pro Trp Phe Leu Leu Asn Lys Ala
        50                  55                  60
Ser Pro Leu Asn Ala Ala Gln Tyr Ala Thr Tyr Thr Lys Leu Val Ala
65                  70                  75                  80
Asp Gln Asn Ala Leu Thr Thr Gln Leu His Thr Phe Cys Ser Ser Ala
                85                  90                  95
Asn Leu Met Cys Ala Pro Asp Leu Ser Pro Ser Leu Glu Lys His Ser
            100                 105                 110
Gly Asp Ile His Phe Ala Thr Tyr Ser Asp Lys Asn Phe Thr Asn Tyr
            115                 120                 125
Gly Thr Asn Glu Pro Gly Ile Gly Val Asn Thr Phe Lys Asn Tyr Ser
            130                 135                 140
Glu Gly Glu Asn Ile Pro Val Asn Ser Phe Arg Arg Tyr Gly Arg Gly
145                 150                 155                 160
Ser Pro Arg Asp Asn Lys Phe Asp Asn Tyr Ala Ser Asp Gly Asn Val
                165                 170                 175
Ile Asp Gln Ser Phe Asn Ser Tyr Ser Thr Ser Thr Ala Gly Gly Ser
            180                 185                 190
Gly Lys Phe Thr Asn Tyr Ala Ala Asn Ala Asn Asp Pro Asn Leu His
            195                 200                 205
Phe Thr Ser Tyr Ser Asp Gln Gly Thr Gly Gly Val Gln Lys Phe Thr
            210                 215                 220
Ile Tyr Ser Gln Glu Ala Asn Ala Gly Asp Gln Tyr Phe Lys Ser Tyr
225                 230                 235                 240
Gly Lys Asn Gly Asn Gly Ala Asn Gly Glu Phe Val Ser Tyr Gly Asn
                245                 250                 255
Asp Thr Asn Val Ile Gly Ser Thr Phe Thr Asn Tyr Gly Gln Thr Ala
            260                 265                 270
Asn Gly Gly Asp Gln Lys Phe Thr Ser Tyr Gly Phe Asn Gly Asn Val
            275                 280                 285
Pro Glu Asn His Phe Thr Asn Tyr Gly Ala Gly Asn Gly Pro Ser
            290                 295                 300
Glu Thr Phe Asn Ser Tyr Arg Asp Gln Ser Asn Val Gly Asp Asp Thr
305                 310                 315                 320
Phe Thr Thr Tyr Val Lys Asp Ala Asn Gly Gly Glu Ala Asn Phe Thr
```

```
                   325                 330                 335
Asn Tyr Gly Gln Ser Phe Asn Glu Gly Thr Asp Val Phe Thr Thr Tyr
                340                 345                 350
Gly Lys Gly Gly Asn Asp Pro His Ile Asn Phe Lys Thr Tyr Gly Val
            355                 360                 365
Asn Asn Thr Phe Lys Asp Tyr Val Lys Asp Thr Ala Thr Phe Ser Asn
        370                 375                 380
Tyr His Asn Lys Thr Ser Gln Val Leu Ala Ser Leu Met Glu Val Asn
385                 390                 395                 400
Gly Gly Lys Lys Val Asn Asn Arg Trp Val Glu Pro Gly Lys Phe Phe
                405                 410                 415
Arg Glu Lys Met Leu Lys Ser Gly Thr Ile Met Pro Met Pro Asp Ile
                420                 425                 430
Lys Asp Lys Met Pro Lys Arg Ser Phe Leu Pro Arg Val Ile Ala Ser
            435                 440                 445
Lys Leu Pro Phe Ser Thr Ser Lys Ile Ala Glu Leu Lys Lys Ile Phe
        450                 455                 460
His Ala Gly Asp Glu Ser Gln Val Glu Lys Met Ile Gly Asp Ala Leu
465                 470                 475                 480
Ser Glu Cys Glu Arg Ala Pro Ser Ala Gly Glu Thr Lys Arg Cys Val
                485                 490                 495
Asn Ser Ala Glu Asp Met Ile Asp Phe Ala Thr Ser Val Leu Gly Arg
                500                 505                 510
Asn Val Val Val Arg Thr Thr Glu Asp Thr Lys Gly Ser Asn Gly Asn
            515                 520                 525
Ile Met Ile Gly Ser Val Lys Gly Ile Asn Gly Gly Lys Val Thr Lys
        530                 535                 540
Ser Val Ser Cys His Gln Thr Leu Tyr Pro Tyr Leu Leu Tyr Tyr Cys
545                 550                 555                 560
His Ser Val Pro Lys Val Arg Val Tyr Glu Ala Asp Ile Leu Asp Pro
                565                 570                 575
Asn Ser Lys Val Lys Ile Asn His Gly Val Ala Ile Cys His Val Asp
            580                 585                 590
Thr Ser Ser Trp Gly Pro Ser His Gly Ala Phe Val Ala Leu Gly Ser
        595                 600                 605
Gly Pro Gly Lys Ile Glu Val Cys His Trp Ile Phe Glu Asn Asp Met
    610                 615                 620
Thr Trp Ala Ile Ala Asp
625                 630

<210> SEQ ID NO 7
<211> LENGTH: 626
<212> TYPE: PRT
<213> ORGANISM: Aradopsis thaliana

<400> SEQUENCE: 7

Met Leu Lys Gln Phe Leu Leu Gln Ser Phe Ser Phe Phe Leu Phe
  1               5                  10                  15
Asn Val Val Ile Val Gly Gly Arg Thr Phe Gly Gly Phe Ser Ala
                20                  25                  30
Glu Glu Asn Pro Phe Thr Pro Lys Ala Ser Leu Val Arg Tyr Trp Asn
                35                  40                  45
Lys Glu Ile Arg Gly Gln Ser Pro Arg Ser Glu Phe Leu Ile Ser Lys
        50                  55                  60
Ala Ser Pro Leu Asn Ala Val Asp Ser Ala Thr Phe Ser Lys Leu Ala
```

```
            65                  70                  75                  80
Ala Ala Asn Ser Leu Pro Thr Arg Phe Pro Asp Phe Cys Ser Ala Ala
                    85                  90                  95

Asn Leu Phe Cys Phe Pro Asp Leu Gly Ala Ser Leu Glu Lys His Asp
            100                 105                 110

Asp Asp Val Lys Phe Ser Val Tyr Asp Gln Lys Asn Phe Thr Asn Tyr
            115                 120                 125

Gly Asn Ala Arg Ala Gly Gly Ala Asp Ser Phe Lys Asn Tyr Ser Lys
            130                 135                 140

Asp Gly Asn Val Val Thr Asp Ser Phe Arg Arg Tyr Ser Arg Asn Ala
145                 150                 155                 160

Ala Gly His Asp Asp Lys Phe Thr Val Tyr Gly Glu Asn Ser Asn Val
                    165                 170                 175

Val Glu Glu Gly Phe Asn Ser Tyr Gly Thr Phe Gly Thr Gly Gly Ala
                    180                 185                 190

Gly Asp Phe Thr Asn Tyr Gln Asn Asn Val Asn Asn Pro Thr Ser Arg
            195                 200                 205

Phe Thr Ala Tyr Ser Asp Gly Gly Asn Gly Arg Ser Gln Thr Phe Lys
            210                 215                 220

Thr Tyr Thr His Glu Ala Asn Ala Gly Asn Gly Gln Ser Phe Thr Ser
225                 230                 235                 240

Tyr Gly Lys Asn Gly Asn Gly Val Pro Asn Glu Phe Thr Ser Tyr Gly
                    245                 250                 255

Val Ser Ser Asn Val Ile Gly Ser Gly Phe Ser Asn Tyr Gly Glu Ser
            260                 265                 270

Gly Asn Ala Ala Asn Asp Thr Phe Thr Ser Tyr Gly Ser Asp Gly Asn
            275                 280                 285

Val Pro Gln Asn Asn Phe Asn Asn Tyr Gly Ala Ser Gly Asn Ala Ala
            290                 295                 300

Val Asp Thr Phe Ala Asn Tyr Arg Asp Lys Ala Asn Val Gly Asp Asp
305                 310                 315                 320

Ser Phe Ser Ser Tyr Ala Lys Asp Ser Asn Ser Glu Lys Val Asn Phe
                    325                 330                 335

Val Asn Tyr Gly Gln Ser Phe Asn Pro Gly Ser Glu Thr Phe Thr Gly
            340                 345                 350

Tyr Gly Lys Gly Ala Glu Gly Ser Lys Leu Ser Phe Lys Thr Tyr Thr
            355                 360                 365

Pro Asn Ser Thr Phe Lys Asp Tyr Ala Lys Lys Gly Val Ala Phe Ala
            370                 375                 380

Lys Tyr Asn Val Ser Thr Thr Ala Asn Thr Val Gly Asp Gly Lys
385                 390                 395                 400

Thr Val Asn Lys Trp Ile Glu Pro Gly Lys Phe Phe Arg Glu Ser Ser
                    405                 410                 415

Leu Lys Glu Gly Thr Val Ile Pro Met Pro Asp Ile Lys Asp Lys Met
            420                 425                 430

Pro Lys Arg Ser Phe Leu Pro Arg Ser Ile Ile Thr Lys Leu Pro Phe
            435                 440                 445

Ser Thr Ser Lys Leu Gly Glu Ile Lys Arg Ile Phe His Ala Val Glu
            450                 455                 460

Asn Ser Thr Met Gly Gly Ile Ile Thr Asp Ala Val Thr Glu Cys Glu
465                 470                 475                 480

Arg Pro Pro Ser Val Gly Glu Thr Lys Arg Cys Val Gly Ser Ala Glu
                    485                 490                 495
```

```
Asp Met Ile Asp Phe Ala Thr Ser Val Leu Gly Arg Ser Val Val Leu
                500                 505                 510

Arg Thr Thr Glu Asn Val Ala Gly Ser Lys Glu Lys Val Val Ile Gly
            515                 520                 525

Lys Val Asn Gly Ile Asn Gly Gly Lys Leu Thr Lys Ala Val Ser Cys
        530                 535                 540

His Gln Ser Leu Tyr Pro Tyr Leu Leu Tyr Tyr Cys His Ser Val Pro
545                 550                 555                 560

Lys Val Arg Val Tyr Glu Ala Asp Leu Leu Glu Leu Asn Ser Lys Lys
                565                 570                 575

Lys Ile Asn His Gly Ile Ala Ile Cys His Met Asp Thr Ser Ser Trp
            580                 585                 590

Gly Pro Ser His Gly Ala Phe Leu Ala Leu Gly Ser Lys Pro Gly Arg
        595                 600                 605

Ile Glu Val Cys His Trp Ile Phe Glu Asn Asp Met Asn Trp Ala Ile
            610                 615                 620

Ala Asp
625

<210> SEQ ID NO 8
<211> LENGTH: 328
<212> TYPE: PRT
<213> ORGANISM: Oryza sativa

<400> SEQUENCE: 8

Met Lys Gly Tyr Met Glu Asp Arg Glu His Glu Lys Ser Leu Gln Ala
  1               5                  10                  15

Glu Lys Glu Glu Leu Lys Glu Val Ser Val Ser Tyr Gly His Glu Val
                 20                  25                  30

Lys Leu Ser Asn Leu Phe Pro Thr Arg Phe Gly His Lys Asn Tyr Gln
             35                  40                  45

His Thr Phe Glu Gly Met Asp His Gly Arg His Val His Ala His Gly
         50                  55                  60

Asn Lys Met Gln Gln Leu Ala Asp Val Phe Phe Arg Asp Ala Leu
 65                  70                  75                  80

Arg Pro Gly Ser Val Ile Thr Pro Thr Ile Pro Pro Thr Thr Ser Leu
                 85                  90                  95

Pro Ala Phe Leu Pro Arg His Val Ala Asp Ala Ile Pro Phe Ser Ala
            100                 105                 110

Asp Arg Phe Ala Asp Val Leu Ala Met Phe Ala Pro Ala Ser Leu Ala
        115                 120                 125

Met Ala Arg Glu Ile Arg Trp Ala Leu Asp Thr Cys Gly Gln Arg Ala
130                 135                 140

Ala Ala Leu Leu Pro Gly Glu Lys Ala Gly Cys Ala Thr Ser Leu Glu
145                 150                 155                 160

Ser Leu Ala Asp Leu Ala Ala Ser Leu Leu Gly Thr Arg Asp Val Arg
                165                 170                 175

Ala Phe Ser Ala Ala Asp Leu Pro Thr Asp Ala Ala Thr Thr Pro Ala
            180                 185                 190

Arg Arg Gly Arg Tyr Asn Val Thr Ser Val Arg Glu Leu Ser Ala Met
        195                 200                 205

Ala Gly Ser Gly Ser Ser Ser Ser Glu Pro Ala Pro Ala Ala Val
    210                 215                 220

Val Ala Cys His Asp Leu Thr Tyr Pro Tyr Ala Val Phe Tyr Cys His
225                 230                 235                 240
```

-continued

```
Ser Thr Lys Pro Thr Ala Ala Tyr Ala Val Thr Leu Val Ala Thr
            245                 250                 255

Thr Gly Asp Gly Asp Gly Glu Gly Glu Ala Ala Ser Pro Ala Lys Met
        260                 265                 270

Glu Ala Leu Ala Val Cys His Leu Asp Thr Ser Arg Trp Arg Ala Asp
    275                 280                 285

Asn Pro Phe Phe Val Ala His Gly Val Lys Pro Gly Glu Val Ser Val
    290                 295                 300

Cys His Phe Leu Thr Lys Leu Ser Ile Val Trp Val Pro Arg His Glu
305                 310                 315                 320

Gln Gly Gly Pro Arg Ala Ala Ala
            325

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
gctagcgcgg tatatcgtca ttgtc                                     25

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
ccgcttttcg acaatccttc ctatc                                     25

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
cgtaactttt gccccttccg ctaatc                                    26

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
cctgggcgtt taacctttcg aatac                                     25

<210> SEQ ID NO 13
<211> LENGTH: 23
<212> TYPE: DNA
<213> ORGANISM: Artificial Sequence
<220> FEATURE:
```

```
<223> OTHER INFORMATION: primer

<400> SEQUENCE: 13
ggctgttcct atctaccgct tcc                                              23

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
agctttgctt acagttcc                                                    18

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
aagttattca agaacagg                                                    18

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
aattaaccct cactaaaggg                                                  20

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
gtaatacgac tcactatagg gc                                               22
```

USE OF GMRD22-LIKE GENES TO PROTECT AGAINST ABIOTIC STRESS

CROSS-REFERENCE TO RELATED APPLICATIONS

This application claims the benefit of U.S. Provisional Ser. No. 60/848,113, filed Sep. 29, 2006. The contents of this document are expressly incorporated herein by reference in its entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 549072000300Seqlist.txt | Mar. 28, 2008 | 31,304 bytes |

TECHNICAL FIELD

This invention relates to agricultural biotechnology. More specifically, this invention relates to novel genes that enhance tolerance to abiotic stresses and uses thereof, particularly in producing transgenic plants, seeds, and progeny thereof that are substantially tolerant of abiotic stress.

BACKGROUND ART

Yield enhancement to increase crop production is one of the essential strategies to meet the demand for food by our continually growing populations. Abiotic stress limits crop production significantly by, e.g., reducing overall crop yield or decreasing crop quality. Abiotic stresses are environmental factors such as drought, salt, extreme temperatures and high winds. While many agricultural practices are designed to optimize crop growth by reducing or avoiding such abiotic stresses, improvements are still needed.

Soybean, one of the most important cash crops, is classified as a moderately NaCl-tolerant plant (Maas & Hoffman, 1977). Understanding the NaCl tolerance mechanism in this crop plant may ultimately help improve its yield on saline lands, and the NaCl tolerance conferring genes in soybean may also be applicable to crops that are more sensitive to NaCl (e.g., carrot, orange and rice). Salinity (accumulation of NaCl) is a severe abiotic environmental stress affecting plant growth. The adverse effects are multifaceted and include ionic stress, physiological drought, specific ion toxicity, and salt-induced oxidative stress. NaCl stress and dehydration stress were long thought to be closely associated since accumulation of salt (mainly NaCl) presents in external environment will lead to a drop of external water potential, which then become lower than that of the water potential in the plant cells. As a result, the net water flow will be from interior of the plant cell to its exterior. This leads to osmotic desiccation (Ashraf, 1994), also known as physiological drought in plants (Jain, et al., 1997).

RD22, first discovered in *Arabidopsis*, is induced by salt stress, but not by cold or heat stress (Yamaguchi-Shinozaki and Shinozaki, 1993). It was found that the plant hormone abscisic acid (ABA) is crucial for the induction of RD22 under dehydration and salt stress, although RD22 lacks the ABA-responsive element (ABRE) (Xiong, et al., 2001). It appears that dehydration triggers the production of ABA, in turns induces expression of various genes, cis- and trans-acting factors. Based on the current model for RD22 induction proposed by Abe and associates (1997), under osmotic stresses (including salt and dehydration stress), ABA is synthesized and triggers the production of RD22BP1 and ATMYB2 proteins, which act as transcriptional activators to bind to the MYC and MYB sites locating on a 67 bp fragment of the RD22 promoter, and hence activates the expression of RD22. However, while the regulation of gene expression of RD22 related to dehydration and salt stress were well studied, its precise role in plant adaptation to salt and dehydration stress remains unknown.

In sum, while gene expression has been correlated to abiotic stresses, a demonstrated ability of such genes to confer tolerance or resistance to such stressors is still lacking. Identification of genes having the ability to significantly alter tolerance to abiotic stress would represent a significant advance for genetic engineering of crops and other plants.

DISCLOSURE OF THE INVENTION

A novel clone impacting tolerance to abiotic stresses, GmRD22, and its related protein, is provided herein. Using suppression subtractive techniques (Diatchenko et al., 1998), provided herein is a novel RD22 clone (GmRD22) originally identified from salt-stressed soybeans. The salt and osmotic stress inducibility in soybeans combined with its protective effect in transgenic rice and *Arabidopsis thaliana* expressing GmRD22 under salt stress suggest that GmRD22 plays a key role in plant adaptive mechanism towards salt and osmotic (and dehydration) stresses. Therefore, GmRD22 and related proteins are useful for genetically engineering crops to improve or confer abiotic stress tolerance.

More specifically, provided herein is an isolated polynucleotide sequence comprising an isolated polynucleotide sequence of SEQ ID NO:1 and complementary sequences thereof. Also provided is an isolated polynucleotide sequence comprising a nucleotide sequence of at least 80%, at least 85%, at least 90%, at least 95% sequence identity to a nucleic acid sequence of SEQ ID NO:1, and complementary sequences thereof.

Further provided is a recombinant nucleic acid construct comprising any one of the polynucleotide provided herein operably linked to control sequences operable to effect detectable expression in plant cells such that tolerance to a particular abiotic stress is induced or increased. In some embodiments, the expression of the heterologous polynucleotide is high. Typically, the control sequences are heterologous to the polynucleotide. In some embodiments, the control sequences further effect insertion of the recombinant nucleic acid construct into host cell chromosomal DNA. Host cells comprising the recombinant nucleic acid construct are provided. In one embodiment, the host cell is a plant cell. Transgenic plant cells as well as transgenic plants comprising the recombinant nucleic acid construct encoding a GmRD22 protein as well as seeds, progeny, and seed of progeny of transgenic plants are also provided.

Provided herein is a substantially pure polypeptide having the amino acid sequence of SEQ ID NO:2, a substantially pure polypeptide having of at least 80%, 90%, or 95% sequence identity to an amino acid sequence of SEQ ID NO:2, and isolated polynucleotide sequences encoding these polypeptides.

Also provided herein is a method for producing the polypeptide comprising growing a host cell under conditions which allow and/or induce the expression of the heterologous polynucleotide and isolating the polypeptide encoded by the polynucleotide.

In one aspect, provided herein is a method to protect plants or plant cells from abiotic stress by inducing or increasing stress tolerance, which method comprises modifying the plants or plant cells to express a heterologous GmRD22 protein, wherein the GmRD22 protein is a polypeptide having of at least 70%, 80%, 90%, 95% or 100% sequence identity to the amino acid sequence of SEQ ID NO:2. The abiotic stress can be salinity (salt) stress or drought (dehydration).

In another aspect, provided herein is a method to protect plants or plant cells from abiotic stress for inducing or increasing tolerance to abiotic stress, which method comprises modifying said plants or plant cells to contain an expression vector comprising a polynucleotide sequence encoding a heterologous GmRD22 protein and operably linked to control sequences operable in plant cells, wherein said GmRD22 protein is a polypeptide encoded by a nucleotide having of at least 70%, 80%, 90%, 95% or 100% sequence identity to the nucleotide sequence of SEQ ID NO:1. In some embodiments, the abiotic stress can be salinity stress or drought.

In yet another aspect, provided herein is method to select for successful transformant of plant cells or plants, which method comprises applying abiotic stress to said plant cells or plants transformed with a recombinant nucleic acid construct or vector comprising an expression system for a GmRD22 protein as a selectable marker, whereby cells that have increased resistance or tolerance to the abiotic stress are selected as successful transformants.

BRIEF DESCRIPTION OF THE DRAWINGS

FIGS. 2A AND 2B shows show the alignment of GmRD22 to other RD22 or BURP-domain containing proteins. The full-length amino acid sequence of GmRD22 (SEQ ID NO:2) was aligned to other identified RD22 proteins, including those from *Arabidopsis*, soybean, rice, tomato and *Brassica napus*. Amino acid residues in bold indicates the BURP-domain conserved among RD22-like proteins. Except for GmRD22, the first two letters of each protein label represent the abbreviated species name, followed by GenBank accession number. At: *Arabidopsis thaliana* (SEQ ID NOS:3, 7); Bn: *Brassica napus* (SEQ ID NO:4); Gm: *Glycine max* (SEQ ID NO:5); Le: *Lycopersicon esculentu* (SEQ ID NO:6)$_m$; Os: *Oryza sativa* (SEQ ID NO:8).

MODES OF CARRYING OUT THE INVENTION

Figure 1:
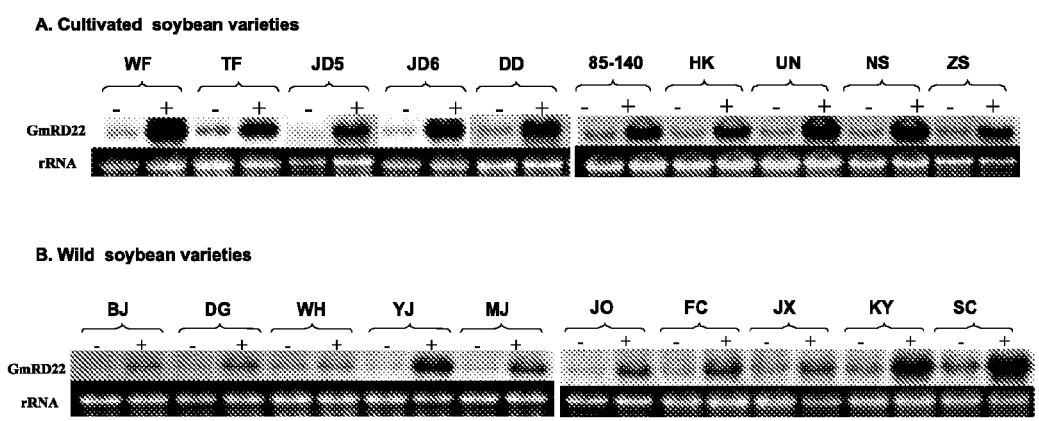
FIGS. 1A AND 1B show the effect of NaCl on the expression of GmRD22 in various cultivated (*G. max*) (A) and wild (*G. soja*) (B) soybean varieties. Seeds of different soybean varieties were germinated and grown as described in Materials and Methods. Twenty-day-old seedlings were subjected to a stepwise NaCl treatment of 0.3%, 0.6% and 0.9% (w/v) in 3-d intervals. Expression of the GmRD22 gene was analyzed by Northern blot analysis after NaCl treatment (see Materials and Methods for details). Ten micrograms of total RNA was loaded onto each lane. + and − indicate plants with and without NaCl treatment, respectively.

Unless otherwise indicated, all technical and scientific terms used herein have the same meaning as they would to one of ordinary skill in the art of the present invention. It is to be understood that this invention is not limited to the particular methodology, protocol, and reagents described, as these may vary.

All publications cited herein are expressly incorporated herein by reference for the purpose of describing and disclosing compositions and methodologies which might be used in connection with the invention.

Heterologous GmRD22 protein expression successfully confers or improves abiotic stress tolerance to plant cells and plants when heterologously expressed, particularly tolerance to salinity and dehydration. The tolerance to abiotic stress is illustrated below in rice and *Arabidopsis thaliana*, but is by no means limited to these examples. Abiotic stress tolerance includes the increased ability to survive in the presence of one or more abiotic stresses. Such abiotic stresses include but are not limited to salinity stress (e.g., hypersalinity), dehydration, high temperatures, low temperatures, freezing temperatures, acidic or alkaline substratum conditions, or growth in the presence of heavy metals or oxidative agents. The precise conditions for an abiotic stress is determined by the type of plant and local environmental conditions for growth.

Thus, provided herein is the novel gene GmRD22, nucleic acid sequence of SEQ ID NO:1 with at least 80% sequence identity to SEQ ID NO:1, and complementary sequences thereof. Also provided is the amino acid sequence of GmRD22 of SEQ ID NO:2 as well as amino acid sequences with at least 80% sequence identity to SEQ ID NO:2. The polynucleotide of GmRD22 may be provided in an integration vector or an expression vector in combination with various promoter constructs to achieve expression of the coding region of GmRD22 in a suitable host plant, plant cell or seed.

Thus, provided herein are isolated or substantially purified nucleic acid or protein compositions for GmRD22. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, (by dry weight) of non-GmRD22 protein. When the GmRD22 protein or a biologically active portion thereof is recombinantly produced, the culture medium typically represents less than about 30%, 20%, 10%, or 5% (by dry weight) of chemical precursors or non-protein-of-interest chemicals.

Fragments and variants of the disclosed polynucleotides or nucleotide sequences are contemplated. Fragments and variants of proteins encoded by the disclosed nucleotide sequences are also provided herein. A fragment is a portion of the nucleotide sequence or a portion of the amino acid sequence. Fragments of a nucleotide sequence may encode protein fragments that retain the biological activity of the native protein and hence induce or increase tolerance to abiotic stress by retaining at least one GmRD22 activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins provided herein.

A fragment of a GmRD22 nucleotide sequence that encodes a biologically active portion of a GmRD22 protein of the invention will encode at least 12, 25, 30, 35, 40, 45, 50, 55, 60, 65, 70, 75, 80, 85, 90, 95, 100, 110, 125, 135, 150, 165, 175, 185, 200, 215, 225, 235, 250, 260, 275, 285, 300, 315, 325, 335, or 340 contiguous amino acids, or up to the total number of amino acids present in a full-length GmRD22 protein of the invention (for example, 343 amino acids for SEQ ID NO:2).

Fragments of a GmRD22 nucleotide sequence that are useful as hybridization probes or PCR primers generally need not encode a biologically active portion of a GmRD22 protein. In some embodiments, a fragment of a GmRD22 encoding nucleotide sequence may encode a biologically active portion of a GmRD22 protein. Nucleic acid molecules that are fragments of a GmRD22 nucleotide sequence comprise at least 16, 20, 25, 30, 40, 50, 60, 70, 80, 90, 100, 125, 150, 175, 200, 225, 250, 300, 350, 400, 450, 500, 550, 600, 650, 700, 750, 800, 850, 900, 950, 1000, or 1025 nucleotides, or up to the number of nucleotides present in a full-length GmRD22 nucleotide sequence disclosed herein.

Provided herein are GmRD22 variant polynucleotides and polypeptides. GmRD22 variants are substantially similar sequences. For nucleotide sequences, conservative variants include those sequences that, because of the degeneracy of the genetic code, encode the amino acid sequence of one of the polypeptides of the invention. Naturally occurring allelic variants such as these can be identified with the use of well-known molecular biology techniques, as, e.g., with polymerase chain reaction (PCR) and hybridization techniques. Variant nucleotide sequences also include synthetically derived nucleotide sequences, such as those generated, for example, by using site-directed mutagenesis but which still encode a GmRD22 protein as provided herein. Generally, variants of a particular nucleotide sequence will have at least 40%, 50%, 60%, 70%, generally at least 75%, 80%, 85%, preferably about 90%, 91%, 92%, 93%, 94%, 95%, 96%, 97%, 98%, 99%, or more sequence identity to that particular nucleotide sequence as determined by sequence alignment programs using default parameters.

A variant GmRD22 protein is a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein as shown in, e.g., SEQ ID NO:2. Variant proteins typically are biologically active, that is, they continue to possess at least one desired biological activity of the full length GmRD22 protein. Such variants may result from, for example, genetic polymorphism or from human manipulation using recombinant molecular biology methods. Biologically active variants of a GmRD22 native protein of the invention will have at least 40%, 50%, 60%, 70%, generally at least 75%, 80%, 85%, preferably about 90%, 91%, 92%, 93%, 94%, 95%, 96%, 97%, 98%, 99%, or more sequence identity to the amino acid sequence for the native protein as determined by sequence alignment programs using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The GmRD22 proteins provided herein may be altered in various ways including amino acid substitutions, deletions, truncations, and insertions. Methods for such manipulations are generally known in the art. For example, amino acid sequence variants of the GmRD22 proteins can be prepared by mutations in the DNA. Guidance as to appropriate amino acid substitutions that do not affect biological activity of the protein of interest may be found in the model of Dayhoff et al. (1979) ATLAS OF PROTEIN SEQUENCE AND STRUCTURE (Natl. Biomed. Res. Found., Washington, D.C.). Conservative substitutions, such as exchanging one amino acid with another having similar properties, may be made.

Thus, the polynucleotide sequences provided herein include both the naturally occurring sequences as well as variant forms. Likewise, the GmRD22 proteins provided herein encompass both naturally occurring proteins as well as variations and modified forms thereof. Such variants will continue to possess at least one of the desired GmRD22-like activities. The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by either an enhanced tolerance to stress when expression of the GmRD22 protein sequence is induced or increased. For example, the activity may be evaluated as an increase in tolerance to hypersalinity in the plant expressing the heterologous GmRD22 protein using the assay described herein.

The GmRD22 polynucleotide sequences provided herein can be used to isolate corresponding sequences from other plants. In this manner, methods such as PCR, hybridization, and the like can be used to identify such sequences based on their sequence homology to the sequences set forth herein. Sequences isolated based on their sequence identity to the entire sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Functions of orthologs are often highly conserved among species. Thus, isolated sequences that encode a GmRD22 protein and which hybridize under stringent conditions to the GmRD22 sequences disclosed herein, or to fragments thereof, are also provided.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the polynucleotide sequences provided herein. Methods for preparation of probes for hybridization and for construction of cDNA and genomic libraries are generally known in the art.

Hybridization of such sequences may be carried out under stringent conditions. Stringent hybridization conditions are those conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, sometimes less than 500 nucleotides in length, less than 200 nucleotides in length, less than 100 nucleotides in length, less than 50 nucleotides in length or 10 to 50 nucleotides in length.

Typically, stringent conditions will be those in which the salt concentration is less than about 1.5 M Na$^+$ ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1×. to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267 284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point $(T_m)$ for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point $(T_m)$; low stringency conditions can utilize a hybridization and/or wash at 11, 12, 13, 14, 15, or 20° C. lower than the thermal melting point $(T_m)$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration may be increased so that a higher temperature can be used.

In general, polynucleotide sequences that encode a GmRD22 protein or a biologically active portion thereof and which hybridize to the GmRD22 sequences disclosed herein will have a sequence identity from about 40% to 50% identical, about 60% to 70% or 75%, and even about 80%, 85%, 87%, 90%, 91%, 92%, 93%, 94%, 95%, 96%, 97%, 98%, or 99% identical, or higher to SEQ ID NO:1, so that the sequences may differ by only one nucleic acid or one amino acid when translated.

Any higher plant or cell of a higher plant is a suitable subject for the present methods including but not limited to tomato, corn, tobacco, rice, sorghum, cucumber, lettuce, turf grass, ornamental (e.g., larger flowers, larger leaves) and legume plants. Such plants can have no endogenous GmRD22 expression or endogenously express GmRD22 protein. Thus, the cells of the transformed plant may comprise a native GmRD22 gene and a recombinant nucleic acid construct encoding an exogenous or heterologous GmRD22 or only a recombinant nucleic acid construct encoding a heterologous GmRD22. Heterologous polynucleotides or nucleic acids are those nucleic acids from a source other than the plant cell into which it is introduced, or into a plant or plant part from which the transgenic part was produced. The heterologous nucleic acid used for transformation can be RNA or DNA, (e.g., cDNA, genomic DNA). In addition, the heterologous nucleic acid can be circular or linear, double-stranded or single-stranded molecules. Single-stranded nucleic acid can be the sense strand or the anti-sense strand.

Any suitable expression vector or recombinant nucleic acid construct system may be employed to modify a susceptible plant cell to contain and express a GmRD22 encoding-polynucleotide. For example, plant cells can be modified to contain nucleotide sequences encoding the relevant protein, optionally operably linked to control sequences operable in plants, or integrated into the genome so as to be expressed under the control of endogenous control sequences. The operably linked sequences are those with a functional linkage between a promoter or promoter-like sequence and a second sequence, wherein the promoter or promoter-like sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

The expression vector system may include in the 5'-3' direction of transcription, a transcriptional and translational initiation region, a GmRD22 DNA sequence as provided herein, and a transcriptional and translational termination region functional in plants. The transcriptional initiation region, the promoter, may be native or heterologous to the plant host. Additionally, the promoter may be an isolated sequence or alternatively a synthetic or recombinant sequence.

Recombinant nucleic acid constructs and expression systems may contain control sequences operable in plants operably linked to the GmRD22 protein-encoding sequence, which control sequences that result in transient, constitutive or inducible expression. Expression can be tissue-specific or tissue non-specific. In some embodiments, a promoter or a fragment of a promoter may be used either alone or in combination with other sequences to create synthetic promoter constructs. In such embodiments, the fragments confer desired properties on the synthetic promoter construct, such as conferring increased transcription of operably linked sequences in response to drought stress or hypersalinity.

Where appropriate, the GmRD22 polynucleotide(s) may be optimized for increased expression in the transformed plant. That is, the genes can be synthesized using plant-preferred codons for improved expression. Methods are available in the art for synthesizing plant-preferred genes. See, e.g., U.S. Pat. Nos. 5,380,831, and 5,436,391.

A wide variety of such control sequences is available in the art, and appropriate vectors for genetic modification are also well known and, indeed, commercially available. The recombinant nucleic acid construct can also include, for example, polyadenylation site, reporter gene and/or intron sequences and the like whose presence may not be necessary for function or expression of the nucleic acid but can provide improved expression and/or function of the nucleic acid by affecting, for example, transcription and/or stability (e.g., of mRNA). Such elements can be included in the recombinant nucleic acid construct to obtain optimal integration and/or expression of the nucleic acid.

In some embodiments of the invention, a polynucleotide encoding the GmRD22 protein is placed in operable linkage with a constitutive promoter and stably integrated into the genome of a suitable host such as rice. Other embodiments include the operable linkage of GmRD22 with developmentally controlled promoters or tissue-specific promoters. Such promoters include leaf-specific, root-specific or seed-specific promoters.

In other embodiments of the invention, a polynucleotide encoding the GmRD22 protein is placed in operable linkage with a chemically-inducible promoter and stably integrated into the genome of or stably expressed in a suitable host plant. In these embodiments, plants which have been subjected to or are at risk for abiotic stress may be treated with the appropriate chemical in order to induce expression of the GmRD22 protein, thereby ameliorating the effect of the stress on the plant and improving crop yield. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters such as the glucocorticoid-inducible promoter and tetracycline-inducible and tetracycline-repressible promoters.

Techniques for effecting genetic modification of plant cells and reconstituting intact plants are now well known in the art. See, e.g., Sambrook et al., MOLECULAR CLONING: A LABORATORY MANUAL, Cold Spring Harbor, N.Y. (1989); Gelvin et al., PLANT MOLECULAR BIOLOGY MANUAL, (1990)); Dashek, METHODS IN PLANT BIOCHEMISTRY AND MOLECULAR BIOLOGY (CRC Press 1997). In one aspect, the promoter can be a 35S CaMV, rice actin promoter, ubiquitin promoter, or nopaline synthase (NOS) promoter. A useful summary of the state of the art in this respect, including a reasonably comprehensive list of the types of plants and plant cells that can form the subjects of the present invention is found in U.S. Patent Publication 2004/0009476, published 14 Jan. 2004, incorporated herein by reference with respect to its disclosure of appropriate techniques for genetic manipulation of plants and the range of plants and plant cells to which these techniques may be applied.

In some embodiments, the expression system or recombinant nucleic acid construct may comprise a selectable marker gene for the selection of transformed cells. Selectable marker genes are utilized for the selection of transformed cells or tissues, and any suitable marker gene can be employed. Marker genes include, include but are not limited to genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). In other embodiments, GmRD22 can act as a selectable marker.

Once transformed plant cells exhibiting tolerance are obtained, transgenic plants can then be regenerated therefrom, and evaluated for stability of the inheritance of the resistance or tolerance trait, that is, whether the resistance or tolerance trait is transmitted to progeny. Thus, provided is a transformed plant that is substantially tolerant or resistant to abiotic stress, particularly salt and drought stress. For example, the plant can survive and/or thrive in the presence of one or more abiotic stressors. The cells of the transformed plant may comprise a native GmRD22 gene as well as a recombinant nucleic acid construct encoding a heterologous GmRD22 polynucleotide sequence or only a recombinant nucleic acid construct encoding a heterologous GmRD22 protein.

Any suitable assay that can assess growth characteristics of any of the transgenic plants provided herein under an abiotic stress condition may be employed. The transmission of abiotic stress tolerant trait can be evaluated at a molecular level, e.g., Southern or Northern blot analysis, PCR-based methodologies, or the biochemical or immunological detection of GmRD22, or by phenotypic analyses, i.e., whether transformed progeny can grow in the presence of salt, drought or other abiotic that inhibits the growth of an untransformed plant. Also provided is a transformed plant seed and other progeny arising from the transformed plant.

Further, because the modified cells and plants provided herein are tolerant to stress caused by dehydration and/or high salinity stress, an expression system comprising a nucleotide sequence encoding the GmRD22 containing protein operably linked to control sequences operable in plants can be used as a selectable marker for successful transformation of cells. Successful transformants are more highly resistant and survive an applied stress for which the marker confers tolerance. Hence, successful transformants can be identified by virtue of their ability to survive and/or thrive under such stress conditions. These stress tolerant "cell lines" can be sub-cultured several times to remove non-tolerant cells.

The GmRD22 transgenic plants, progeny and seeds provided herein also may be employed alone or in combination with other water conserving agricultural practices to reduce or limit the usage of water while maintaining crop yield and quality. In particular, these plants, progeny and seeds are particularly useful in saline lands and arid/semi-arid regions as the induced or increased tolerance to abiotic stressors will permit these transgenic plants to thrive in lands otherwise unusable or undesirable for agricultural development.

The following examples are offered to illustrate but not to limit the invention.

Example

Figure 2A:
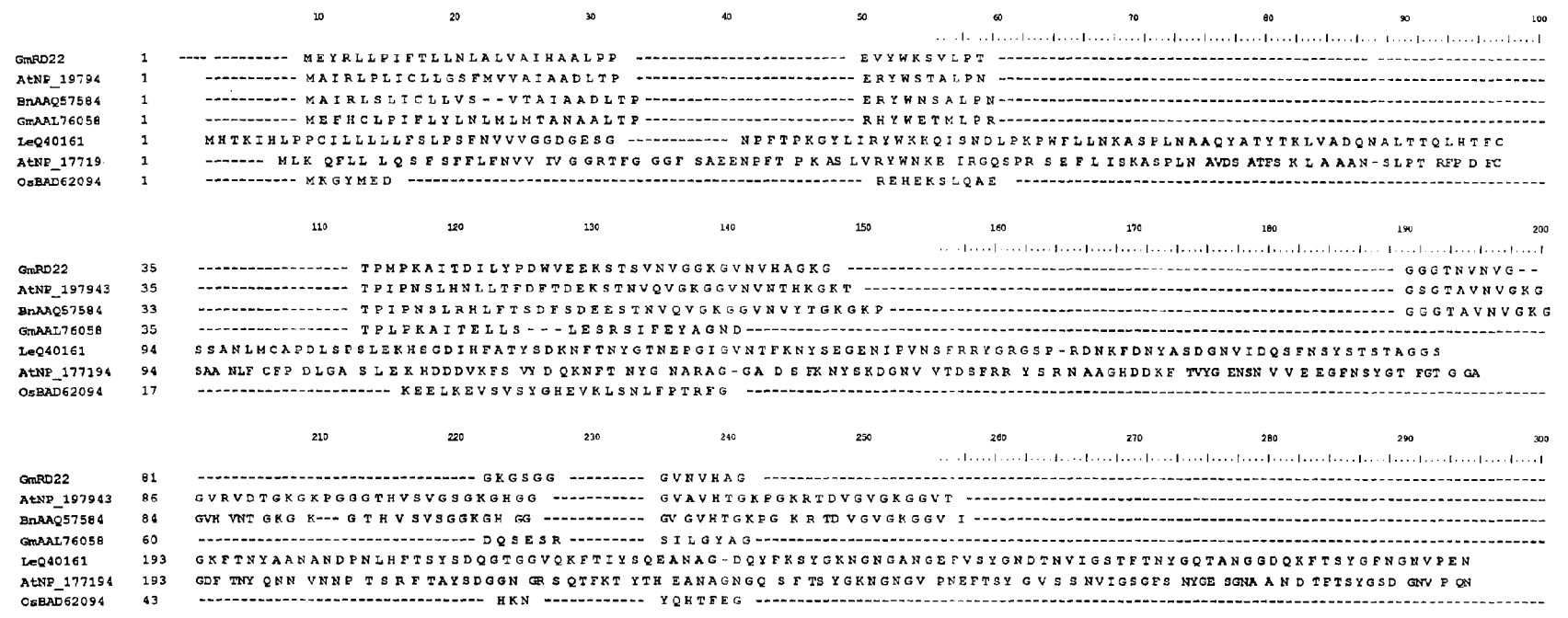
Figure 2B:
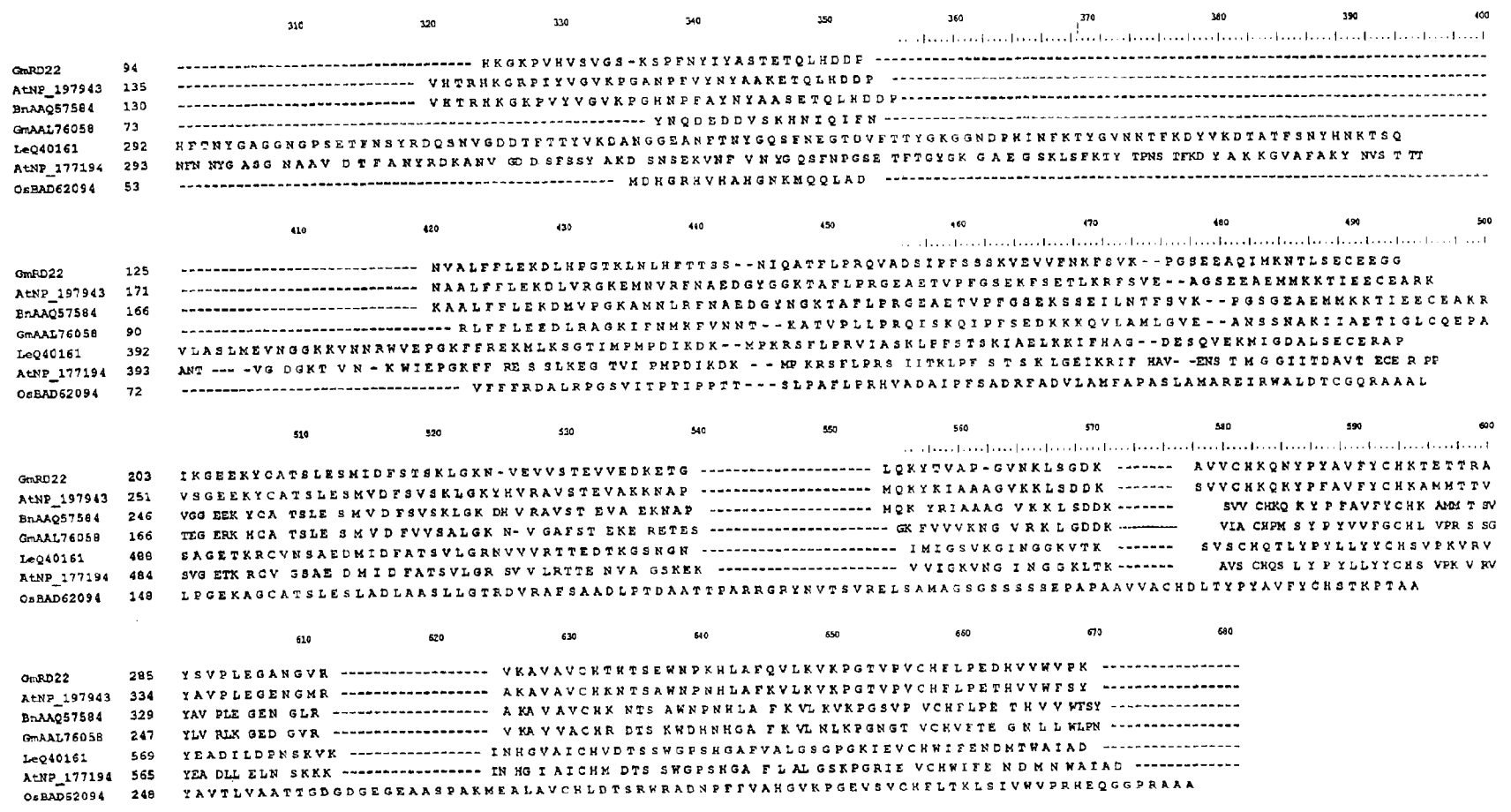
Figure 3:
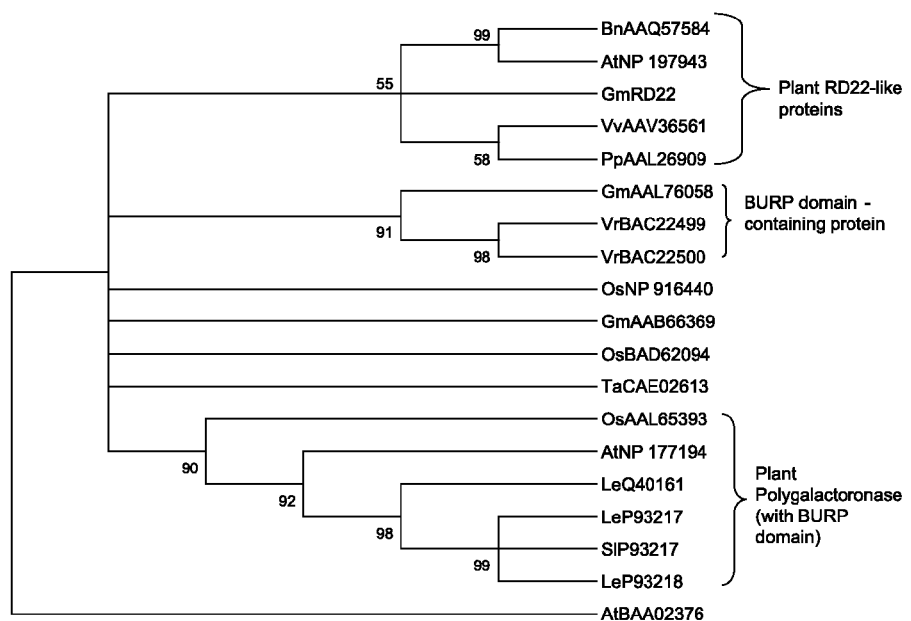
FIG. 3 shows the phylogenetic analysis of RD22 proteins and other BURP domain containing proteins. Phylogenetic relationship of plant RD22 proteins, including GmRD22 was analyzed using the ClustalW and MEGA (version 2.1) programs (Thompson et al., 1994; Kumar et al., 2001). *Arabidopsis* RD29A (accession no. BAA02376) was used as an outgroup. The analyzed polypeptides were divided into three major groups, including: plant RD22 proteins (Group I), resistance related protein with BURP domain and plant polygalactoronase (with BURP domain). Bootstrap values were indicated for major branches as percentages. One thousand replicates were used for all possible tree topology calculation. Except for GmRD22, the first two letters of each protein label represent the abbreviated species name, followed by GenBank accession number. At: *Arabidopsis thaliana*; Bn: *Brassica napus*; Gm: *Glycine max*; Le: *Lycopersicon esculentum*; Os: *Oryza sativa*; Pp: *Prunus persica*; Vr: *Vigna radiate*; Vv: *Vitis vinifera*.

Identification of Salt Stress Responsive Genes in Salt Tolerant Soybean Germplasms Suppression subtractive hybridization (SSH) techniques (see Materials and Methods) were used to identify salt-inducible genes from the soybean variety Wenfeng 7. The full-length coding regions of selective fragments were obtained by 5' and 3'-RACE. One of the candidate genes (GmRD22) was found to be strongly induced by NaCl stress in all the ten cultivated and ten wild soybean varieties tested (FIGS. 1A and 1B). DNA sequence analysis indicated that GmRD22 was a RD22-like gene due to the high homology of its gene product to other identified plant RD22 gene products, as well as some BURP domain-containing protein. BURP domain is a conserved domain found at the C-terminus of several plant proteins including RD22 proteins. The putative peptide of GmRD22 shares 66% homology to RD22-like protein from *Vitis vinifera,* 65% homology to dehydration-induced protein RD22-like protein from *Gossypium hirsutum,* and 63% to a BURP protein from *Medicago truncatula.* Moreover, the BURP domain that found in other identified RD22 proteins is conserved in GmRD22 (FIGS. 2A and 2B). The phylogenetic relationship of the GmRD22 polypeptide to other RD22-like protein/BURP domain-containing protein was analyzed using the ClustalW (Thompson et al., 1994) and MEGA (version 2.1) program (Kumar et al., 2001). RD29A from *Arabidopsis* was used as an outgroup. In the Neighbor-joining tree of RD22 proteins, GmRD22 together with other published plant RD22 proteins form a tight group (FIG. 3).

Figure 4:
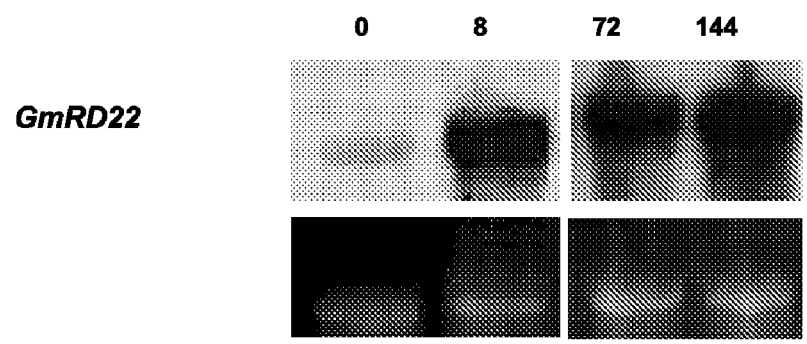
FIG. 4 shows the expression of GmRD22 in soybean leaves under NaCl stress. The short-term and long-term effects of NaCl treatments on the expression of GmRD22 in soybean leaves were studied by Northern blot analysis (see Materials and Methods). Surface-sterilized seeds were germinated in filter papers containing modified Hoagland's solution. After germination, 1-week-old seedlings of uniform growth stage were transferred to a hydroponics system containing the same culture medium. After opening of the first trifoliates, the seedlings were treated with Hoagland's solution supplemented with 125 mM NaCl. The youngest fully expanded trifoliate leaves of treated plants were collected for total RNA extraction after 0-, 8-, 72- and 144-h treatment. Ethidium bromide staining of rRNA was used as a loading reference for RNA samples.
Figure 5:
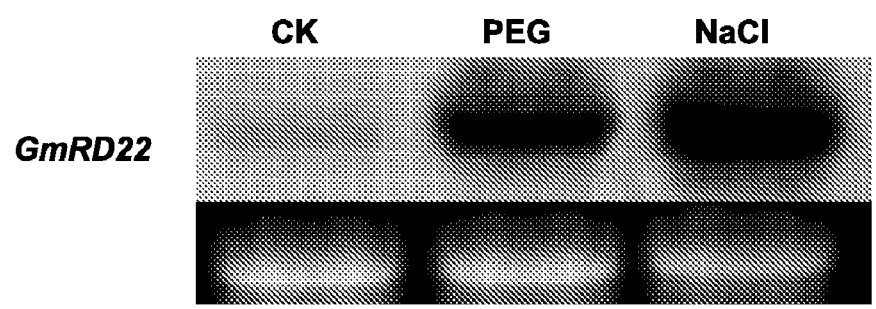
FIG. 5 shows a Northern blot analysis of GmRD22 under salt and PEG treatment. Growth conditions and treatments were as described in Materials and Methods. CT: Control, NaCl: 125 mM NaCl treatment for 48 hr; PEG: 5% PEG treatment for 48 hr, which mimic the effect of dehydration. 10 µg of total RNA was loaded onto each lane.

The expression of GmRD22 under NaCl stress was studied using Northern blot analysis. When soybean plants were subjected to a short-term NaCl treatment (up to 8 h), an initial rise of GmRD22 mRNA levels were observed 8 h after treatment (FIG. 4). In parallel, the accumulation of $Na^+$ in leaves was minimal during the first 8 h after treatment. Therefore, the initial rise of GmRD22 mRNA levels may be a result of dehydration responses. When soybean plants were subjected to long-term NaCl treatment (over 72 h), the steady-state mRNA levels of GmRD22 remained high (FIG. 4). To further explore the possible regulation of GmRD22 gene expression by dehydration, soybean plants were subjected to PEG treatment to mimic the dehydration stress (Jia et al., 2001). When soybean plants were subjected to long-term salt or dehydration treatment, the steady-state mRNA level of GmRD22 was elevated (FIG. 5).

Figure 6:
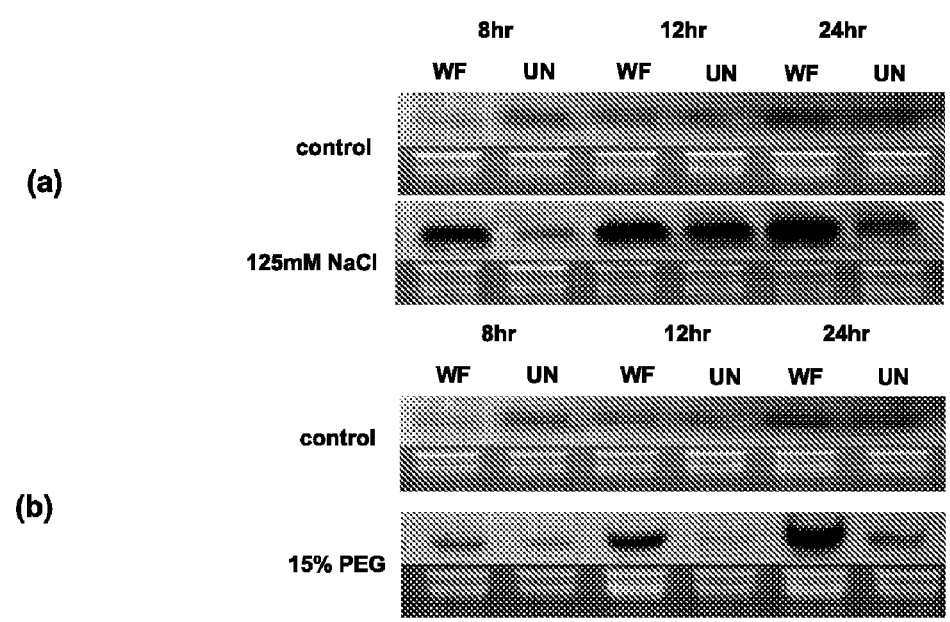
FIGS. 6a AND 6b shows show differential expression pattern of GmRD22 among 2 soybean cultivars with contrasting salt tolerance ability under: (a) salt stress and (b) osmotic stress. Growth conditions and treatments were as described in Materials and Methods. WF: the salt tolerant cultivar Wenfeng 7; UN: the salt sensitive cultivar Union. 10 µg of total RNA was loaded onto each lane.

To further characterize the function of GmRD22 in response to salt and dehydration stress, the stress conditions that may affect the expression of GmRD22 were determined using 2 genetically distinct soybean varieties: WF (a salt-tolerant variety) and UN (a salt-sensitive variety). Gene expression profile of GmRD22 in response to salt, dehydration and ABA treatment at different time point was studied using Northern blot analysis. Interestingly, after 8 hr of salt treatment, GmRD22 showed differential induction in the salt tolerant cultivar (WF) when compared to the salt sensitive (UN) one under both salt and dehydration treatment. Such phenomenon also was observed in longer term treatments (12 and 24 hr) (FIGS. 6a and 6b).

Figure 7:
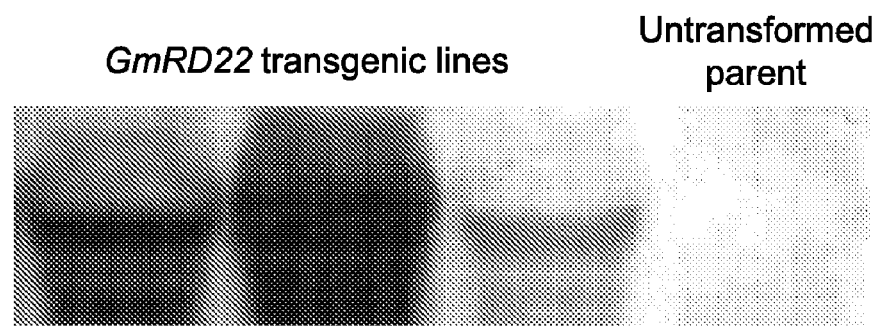
FIG. 7 shows the expression of GmRD22 in transgenic rice using Northern blot analysis. All 3 independent transgenic lines show expression of GmRD22 while the untransformed parent gives no signal.
Figure 8:
FIG. 8 shows a field test of GmRD22 transgenic rice. The transgenic rice together with the wild type were planted in the open field and treated with 2% salt water (in the form of sea water). After treated for a month, transgenic rice harboring GmRD22 or one other proprietary clone obtained in our lab still survived while most of the others (including the parental line Nipponbare) failed to sustain in such a harsh environment.
Figure 8:
Figure 9:
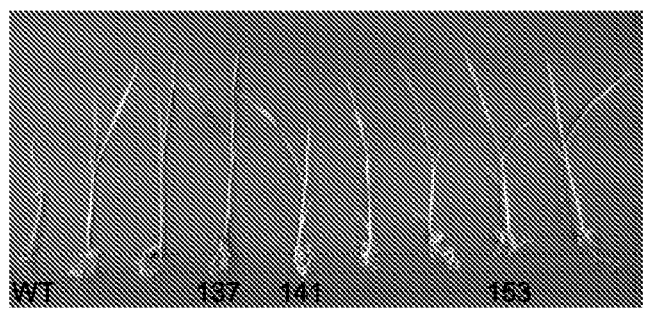
FIGS. 9a AND 9b shows show the performance of several homozygous GmRD22 transgenic rice lines and the untransformed wild type under: (a) drought stress and (b) salinity stress. Growth conditions and treatments were as described in Materials and Methods. WT: wild type; 137, 141, 153: GmRD22 transgenic lines. The seedlings without label are transgenic rice expressing another proprietary clone (also confers salt and drought tolerance) obtained in our lab. For drought stress experiment, the GmRD22 transgenic rice could recover by replenishing liquid medium after the removal for 16 hours. Under such conditions, the wild type could not survive. For salinity stress experiment, the GmRD22 transgenic rice but not the wild type could survive in 200 mM NaCl.
Figure 9:
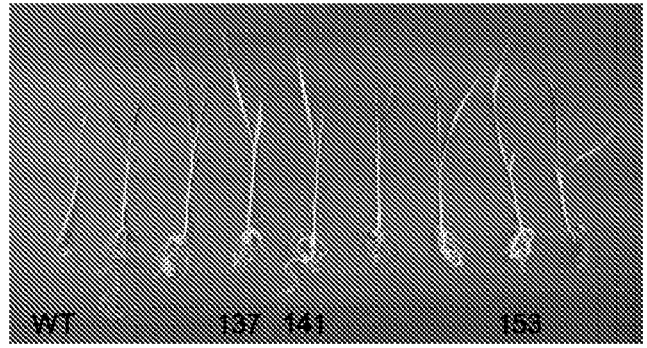
Figure 10:
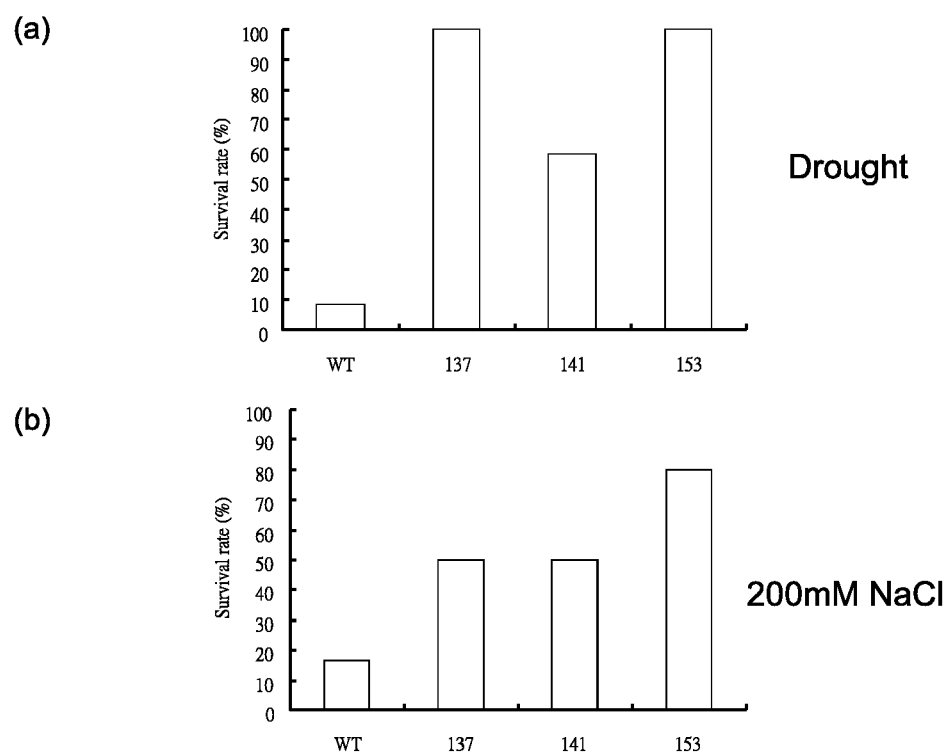
FIGS. 10a AND 10b show the survival rates of GmRD22 transgenic rice and the untransformed wild type under: (a) drought stress and (b) salinity stress. Growth conditions and treatments were as described in Materials and Methods and FIGS. 9a and 9b. WT: wild type; 137, 141, 153: GmRD22 transgenic lines. The GmRD22 transgenic rice exhibits higher survival rate than the untransformed wild type.

Transgenic rice expressing GmRD22 were constructed. Northern blot analysis was performed to confirm the expression of GmRD22 and all transgenic lines tested showed expression of the transgene (FIG. 7). The transgene conferred salt tolerance to rice in testing saline field and was found to be able to survive under 2% salt treatment (FIG. 8). Also, homozygous GmRD22 transgenic rice lines, in a growth chamber setting, could confer tolerance to drought stress and salinity stress (FIGS. 9a and 9b). The drought stress was achieved by removal of liquid growth medium for 16 hours followed by replenishment. The salinity stress was achieved by an addition of 200 mM NaCl into the liquid growth medium. Under either drought stress or salinity stress, transgenic rice expressing GmRD22 exhibited a much better survival rate (FIGS. 10a and 10b).

Figure 11:
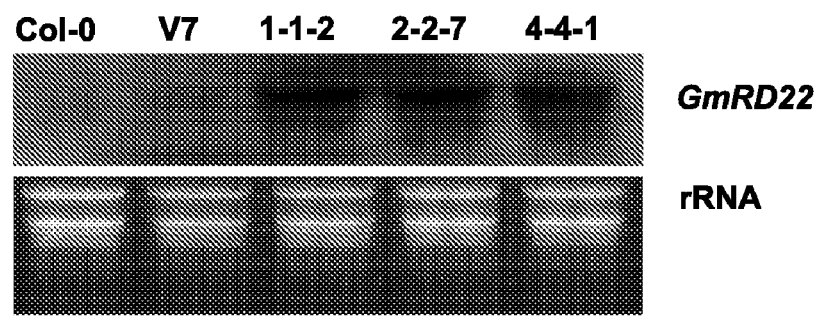
FIG. 11 shows the expression of GmRD22 in transgenic *Arabidopsis thaliana* using Northern blot analysis. Col-0: wild type parent; V7: an empty vector transgenic control. 1-1-2, 2-2-7, 4-4-1: three independent GmRD22 transgenic lines. Strong signals can be seen in all independent transgenic lines. The very faint signals in Col-0 and V7 are probably due to the endogenous *Arabidopsis* RD22 transcripts.
Figure 12:
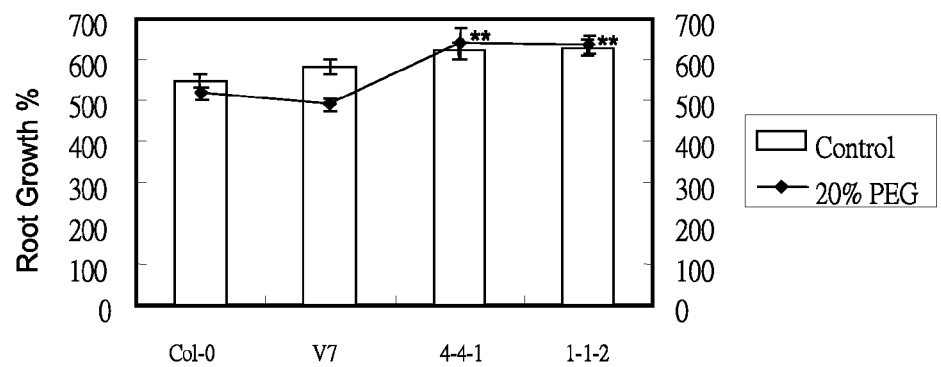
FIG. 12 shows the effects of osmotic stress on root growth of GmRD22 transgenic *Arabidopsis thaliana*. The percentage of root growth after treated with 20% PEG was compared among the wild type Col-0, the empty vector transgenic control (V7) and two independent GmRD22 transgenic lines (4-4-1 and 1-1-2). Y-axis on the left and right of the graph indicated the % root growth of untreated (bar) and stressed (line) plants, respectively. Error bar: standard error. N=16. Data obtained were analyzed by one-way analysis of variance (one-way ANOVA) followed by the Tukey's test. ** indicates that the mean difference (compared to wild type) is significant at $p<0.01$ level.
Figure 13:
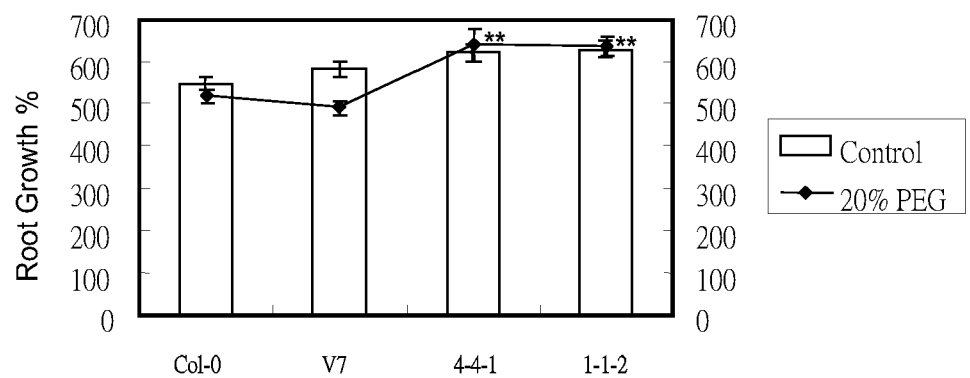

Transgenic Arabidopsis expressing GmRD22 were constructed. Northern blot analysis was performed to confirm the expression of GmRD22 and all transgenic lines tested showed expression of the transgene (FIG. 11). When subjected to osmotic stress (20% PEG), the GmRD22 transgenic Arabidopsis lines exhibited a better root growth than the untransformed wild type (Col-0) and the empty vector transgenic control (V7) (FIG. 12).

Transgenic rice expressing GmRD22 were constructed. The transgenic rice was found to be able to survive under 2% salt treatment. The transgene conferred salt tolerance to rice in testing saline field (FIG. 8). Northern blot analysis was performed to confirm the expression of GmRD22 and all transgenic lines being tested shown expression of the transgene (FIG. 7).

In a search for salt-inducible genes in soybean using subtraction subtractive hybridization techniques, a novel RD22-like gene, namely GmRD22, was cloned. Several lines of evidences suggest that it was indeed a member of the RD22 family: (1) It exhibits high homology to other identified RD22 proteins; (2) by phylogenetic analysis it form a tight group together with the other identified plant RD22-like proteins.

GmRD22 functioned in the adaptation to NaCl and dehydration stress. When soybean plants were treated with NaCl, physiological drought is the immediate stress. As a result of physiological drought, the leaves drooped within 1 h and the stomatal conductance dropped to less than 50% of the baseline within 10 min after NaCl treatment (data not shown). A prominent induction of GmRD22 mRNA levels in leaves started to appear within 8 h after NaCl treatment (FIG. 4) when no significant accumulation of $Na^+$ in leaves was established at this time. When subjected to long-term NaCl treatments, expression of GmRD22 remained at a high expression level (FIG. 4). Because dehydration symptoms were also observed in leaves when soybean plants were placed under such long-term treatments, we could not distinguish whether the apparent NaCl induction effects were results of NaCl per se or whether the consequential drought was caused by stress. The induction of GmRD22 by PEG (FIG. 5) further supported the notion that the gene expression of GmRD22 was at least in part regulated by dehydration.

In the comparative studies using 2 soybean germplasms with contrasting salt-tolerance ability, GmRD22 showed a differential induction in the salt tolerance cultivar (WF) when compared to the salt sensitive (UN) one under both salinity stress and osmotic stress (FIGS. 6a and 6b).

Transgenic rice and Arabidopsis thaliana were used to perform gain-of-function tests to investigate the possible application value of GmRD22 in stress-tolerance crops engineering. Transgenic rice expressing GmRD22 (FIG. 7) survived under 2% salt treatment (in form of sea water) in a field test (FIG. 8), but not for the untransformed parent. When grown in environmental controlled growth chambers, GmRD22 transgenic rice showed a higher recovery and survival rates under drought stress and salt stress (FIG. 9a-b and 10a-b). Similar protection was also observed in transgenic Arabidopsis thaliana expressing GmRD22 (FIG. 11). Transgenic GmRD22 Arabidopsis thaliana exhibited a higher growth rate in root under drought stress when comparing to the untransformed wild type (Col-0) and the empty vector transgenic control (V7) (FIG. 12). These findings demonstrated that GmRD22 was able to protect the plant from salinity, salinity-induced dehydration, and drought stresses.

In sum, the NaCl and PEG inducibility of GmRD22 showed that its physiological role was related to the adaptation to salinity, salinity-induced dehydration, and drought stresses. Expressing GmRD22 in rice and Arabidopsis thaliana provided definitive evidence that heterologous expression protects plants from salinity and drought stresses, suggesting that this clone can be used for salt tolerant and drought tolerant crop engineering.

Materials and Methods

Plant materials. Ten cultivated (*Glycine max* L. *Merr.*) and ten wild (*Glycine soja*) soybean varieties consisting of different genetic backgrounds were employed in this study. The cultivated varieties Union (UN), Hark (HK) and Nebsoy (NS) are from the U.S.A. The other cultivated varieties Wenfeng 7 (WF), Tiefeng 8 (TF), Jindou 5 (JD5), Jindou 6 (JD6), Dandou 5 (DD), 85-140 and Zaoshu 6 (ZS) are from P.R.C. All wild soybean varieties including: Beijing 4 (BJ), Donggou 16 (DG), Wuhai 4 (WH), Yinjin3 (YJ), Mengjin 1 (MJ), Jidong 5 (JO), Fengcheng 20 (FC), Jixian 11 (JX), Kaiyuan 21 (KY) and Shuangcheng 4 (SC) are originated from P.R.C. The rice transformation parent was Oryza sativa, sub-species japonica, variety Nipponbare. The Arabidopsis thaliana transformation parent was the ecotype Col-0.

Molecular cloning, phylogenetic analysis, and gene expression study of a RD22-like gene from soybean. To prepare samples for the construction of the subtractive library, seeds of the variety Wenfeng7 (WF) were germinated and grown in perforated plastic pots filled with thoroughly washed silicon sand and irrigated with modified Hoagland's nutrient solution (Hoagland and Amon, 1938) for 14 days before treated with 0.3% (w/v) NaCl for 3 days. The salt treatment was then gradually increased to 0.6%, 0.9%, 1.2%, and finally to 1.5% (w/v) NaCl in 3-day intervals, total RNA was extracted from the leaves of NaCl-treated and control seedlings using a modified phenol/chloroform/isoamylalcohol (P:C:I=25:24:1, v/v) mediated extraction protocol (Jackson and Larkins, 1976). The CLONTECH PCR-Select cDNA Subtraction Kit (Clontech K1804-1) was employed to construct the WF subtractive library. All procedures were performed according to the manufacturer's recommendations. The tester and driver cDNAs were originated from the leaves of NaCl-treated and control WF plants, respectively. Selected subtractive fragments were cloned into the pBluescript II KS (+) by the T-A cloning method (Sambrook and Russell, 2001). The ligation products were then transformed into the *Escherichia coli* strain DH5α by the $CaCl_2$ method (Sambrook and Russell, 2001). The cDNA clone in each successful transformant was sequenced using the ABI PRISM™ dRhodamine Terminator Cycle Sequencing Ready Reaction Kit (Perkin Elmer 402078). Prepared sequencing samples were applied to the Genetic Analyzer ABI prism 310 to resolve the cycle sequencing product. All sequencing data were analyzed by Blastn, Blastx and PSI-Blast programs provided on the National Center for Biotechnology Information website. One of the subtractive fragments (GmRD22) was identified as a RD22-like gene based on its high homology to other known RD22 and RD22-like genes (see Results). The cDNA sequence covering the intact coding region of GmRD22 was first obtained by 5' and 3' rapid amplification of cDNA ends (RACE) techniques using the SMAR™ RACE cDNA amplification Kit (Clontech K1811-1). For 5'RACE, the gene specific primers were as follows: GSP1 (5'-GCTAGCGCGGTATATCGTCATTGTC) (SEQ ID NO:9); nested-GSP1 (5'-CCGCTTTTCGACAATCCTTCCTATC) (SEQ ID NO:10); and nested-GSP2 (5'-CGTAACTTTTGC-CCCTTCCGCTAATC) (SEQ ID NO:11). For 3'RACE, the gene specific primers were as follows: GSP1 (5'-CCTGGGCGTTTAACCTTTCGAATAC) (SEQ ID NO:12) and nested-GSP1 (5'-GGCTGTTCCTATCTACCGCTTCC) (SEQ ID NO:13). Touch-down polymerase chain reaction (PCR) reactions for RACE were performed according to the manufacturer's instruction with modification in the annealing temperatures as follows: amplification with 5' and 3' GSP1 (70° C., 68° C. and 66° C. for $1^{st}$, $2^{nd}$ and $3^{rd}$ round PCR, respectively); reamplification with 5' nested-GSP1, 5' nested-GSP2 and 3' nested-GSP1 (70° C. and 67° C. for $1^{st}$ and $2^{nd}$ round PCR, respectively). The DNA sequence of GmRD22 was subsequently verified by direct sequencing of the PCR products generated from a WF cDNA preparation using primers flanking the full-length coding region of GmRD22 (5'-AGCTTTGCTTACAGTTCC (SEQ ID NO:14) and 5'-AAGTTATTCAAGAACAGG) (SEQ ID NO:15).

Phylogenetic relationships of GmRD22 with other RD22-like proteins/BURP domain containing proteins were analyzed. Multiple sequence alignment was performed using the ClustalW program (Thompson et al., 1994). The bootstrap value was calculated and the phylogenetic tree was built using the MEGA program (version 2.1) (Kumar et. al., 2001). One thousand replicates were used for all possible tree topology calculations.

To prepare RNA samples for the NaCl inducibility test, seeds of different soybean varieties were germinated and grown as described above. Gene expression was analyzed by Northern blot analysis using a standard procedure in a hybridization solution containing 50% formamide at 42° C. (Sambrook and Russell, 2001). Single-stranded DIG (Digoxigenin)-labeled PCR products were used as probes (Finch et al., 1991). T3 and T7 primers (5'-AATTAACCCTCAC-TAAAGGG (SEQ ID NO:16) and 5'-GTAATACGACTCAC-TATAGGGC (SEQ ID NO:17)) flanking the original subtractive GmRD22 clone were employed to generate probes for GmRD22.

Growth conditions for NaCl stress and dehydration stress. For NaCl treatments, the surface sterilized seeds were germinated in filter papers containing modified Hoagland's solution. After germination, 1-week-old seedlings of uniform growth stage were transferred to a hydroponics system containing the same culture medium. After the opening of the first trifoliate, the seedlings were treated with Hoagland's solution supplemented with 125 mM NaCl. The youngest fully expanded trifoliate of treated plants were collected for total RNA extraction after 0-, 8-, 72- and 144-h treatment. For polyethylene glycol (PEG) treatment, the soybean plants were germinated and grown similarly, except that the resulting seedlings were treated with Hoagland's solution (control) or Hoagland's solution supplemented with 5% PEG 6000 or 125 mM NaCl. The youngest fully expanded trifoliate was collected for total RNA extraction after 48-h treatment. The youngest fully expanded trifoliate was collected for total RNA extraction after 8-, 12- and 24-h after treatment. Gene expression was analyzed by Northern blot analysis using a standard procedure in a hybridization solution containing 50% formamide at 42° C. (Sambrook and Russell, 2001). Single stranded DIG (Digoxigenin)-labeled PCR products were used as probes (Finckh et al., 1991). T3 and T7 primers (5'-AATTAACCCTCACTAAAGGG (SEQ ID NO:16) and 5'-GTAATACGACTCACTATAGGGC (SEQ ID NO:17)) flanking the original subtractive GmRD22 clone were employed to generate probes for GmRD22.

Establishment of transgenic rice lines. The construction of transgenic rice is a joint effort with the China National Rice Institute. The transgene were cloned into the multiple cloning site (MCS) of the double T-DNA binary vector pSB 130 driven by the ubiquitin promoter. The *Oryza sativa* ssp *japonica* cultivar Nipponbare was used to induce callus for transformation. The constructs containing the target gene were transformed into calli by co-cultivation. The transformed calli, after subsequent sub-culturing, were regenerate on regeneration medium with hygromycin as selective agent. The transformants were screened for presence of transgene by PCR using Gene-specific primer. The transgenic lines were screened and raised until homozygous lines obtained. Northern blot analysis was performed to confirm expression of transgene.

Growth conditions for effects of salt stress in transgenic rice in open field. After germination, rice seedlings were sowed into the open field and treated with 2% salt water for 1 month.

Growth conditions for effects of drought stress and salt stress in transgenic rice in environmental-controlled growth chamber. After germination in the dark for 10 days, triplicate sets each containing the wild type parent and three independent GmRD22 transgenic rice lines were grown in ½ MS liquid medium for another 9 days, in a growth chamber kept at about 28° C. with a 16 h light (intensity about 120 µE)-8 h dark cycle. The first group was treated with ½ MS liquid medium supplemented with 200 mM NaCl for 2 days followed by irrigation of ½ MS liquid medium for 2 days. Drought stress was introduced to another group by the removal of the liquid growth medium for 16 hours followed by replenishment of ½ MS liquid medium for 3 days. The control group was irrigated with ½ MS liquid medium throughout the whole testing period. The performance of the representative seedlings was recorded and survival rates were calculated.

Establishment of transgenic *Arabidopsis* lines. The transgene was subcloned into the multiple cloning site (MCS) of the binary vector V7 (Brears, et al., 1993) driven by the CaMV $^{35}$S constitutive promoter. The transformation was carried by *Agrobacterium*-mediated method aided with vacuum infiltration (Bechtold and Pelletier, 1993). The positive transformants were selected by kanamycin and the presence of transgene was confirmed by PCR using GmRD22-specific primers. The transgenic lines with single insertion locus were screened and propagated until homozygous lines were obtained. Northern blot analysis was performed to confirm the expression of transgene.

Testing the effects of drought stress on the root length of transgenic *Arabidopsis*. Seeds from the wild type parent (Col-0), the empty vector transgenic control (V7) and two independent GmRD22 transgenic lines (4-4-1 and 1-1-2) were sown on MS plates containing 3% sucrose and 0.9% (w/v)

agar. Seedlings (7 d after germination) were transferred onto either the control MS agar plates or MS agar plates supplemented with 20% polyethylene-glycol 6000 (PEG). The root length of each individual seedlings before and 7 d after treatment was recorded and percentage root growth was calculated.

REFERENCES

Abe, H., Yamaguchi-Shinozaki, K., Urao, T., Iwasaki, T., Hosokawa, D., and Shinozaki, K. (1997). Role of *Arabidopsis* MYC and MYB homologs in drought and abscisic acid-regulated gene expression. *Plant Cell* 9, 1859-68

Ashraf, M. (1994) Breeding for salinity tolerance in plants. *Crit. Rev. Plant Sci.* 13, 17-42

Bechtold, N. and Pelletier, G. (1993). In planta *Agrobacterium*-mediated transformation of adult *Arabidopsis thaliana* plants by vacuum infiltration. In: Martinez-Zapater, J., Salinas, J. (Eds.), ARABIDOPSIS PROTOCOLS. Humana Press Inc., Totowa, pp. 259-266.

Brears, T., Liu, C., Knight, T. J. and Coruzzi, G. M. (1993). Ectopic overexpression of asparagines synthetase in transgenic tobacco. *Plant Physiol.* 103: 1285-90.

Diatchenko, L., Chenchik, A. and Siebert, P. (1998). Suppression subtractive hybridization: A method for generating subtracted cDNA libraries starting from poly (A+) or total RNA. In: Siebert, P., Larrick, J. (Eds.), RTPCR METHOD FOR GENE CLONING AND ANALYSIS. Eaton Publishing, Natick, Mass., pp. 213-39.

Finckh, U., Lingenfelter, P. A., Myerson, D. (1991). Producing single-stranded DNA probes with the Taq DNA polymerase: a high yield protocol. *Biotechniques* 10: 35-38.

Hoagland, D. R. and Arnon, D. I. (1938). The water-culture method for growing plants without soil. *Calif. Agric. Expt. Circ.* 347, 1-39.

Jackson, A. O. and Larkins, B. A. (1976). Influence of ionic strength, pH, and chelation of divalent metals on isolation of polyribosomes from tobacco leaves. *Plant Physiol.* 57, 5-10.

Jain, R. L., and Selvaraj, G. (1997). Molecular genetic improvement of salt tolerance in plants. In *Biotechnology Annual Review* (El-Gewely, M. R., ed) Vol. 3 pp. 245-67, Elsevier Science B. V.

Kumar, S., Tamura, K., Jakobsen, I. B. and Nei, M. (2001). MEGA2: molecular evolutionary genetics analysis software. *Bioinformatics* 17, 1244-45.

Maas, E. V., and Hoffman, J. G. (1977). Crop salt tolerance-current assessment. *J. Irrig. Drain. Eng.* 103:115-34.

Sambrook, J. and Russell, D. W. (2001). MOLECULAR CLONING: A LABORATORY MANUAL, Ed 3rd. Cold Spring Harbor Laboratory Press, New York.

Thompson, J. D., Higgins, D. G., and Gibson, T. J. (1994). CLUSTALW: improving the sensitivity of progressive multiple sequence alignment through sequence weighting. position-specific gap penalties and weight matrix choice. *Nucleic Acids Res.* 22, 4673-680.

Xiong, L. M., Ishitani, M., Lee, H. J., and Zhu, J. K. (2001). The *Arabidopsis* LO35/ABA3 locus encodes a molbdenum cofactor sulfurase and modulated cold stress- and osmotic stress-responsive gene expression. *Plant Cell* 13, 2063-83.

Yamaguchi-Shinozaki, K., and Shinozaki, K. (1993). The plant hormone abscisic acid mediated the drought-induced expression but not the seed-specific expression of rd22, a gene responsive to dehydration stress in *Arabidopsis thaliana. Mol. Gen. Genet.* 238, 17-25.

Modifications may be made to the foregoing without departing from the basic aspects of the invention. Although the invention has been described in substantial detail with reference to one or more specific embodiments, those of skill in the art will recognize that changes may be made to the embodiments specifically disclosed in this application, yet these modifications and improvements are within the scope and spirit of the invention, as set forth in the claims which follow.

Citation of the above publications or documents is not intended as an admission that any of the foregoing is pertinent prior art, nor does it constitute any admission as to the contents or date of these publications or documents. U.S. patents and other publications referenced herein are hereby incorporated by reference.

---

The invention claimed is:

1. A method of producing a transgenic plant having an increased tolerance to salt stress, said method comprising the steps of:
   (a) transforming plant cells with a recombinant nucleic acid construct comprising a polynucleotide sequence which comprises a nucleotide sequence encoding an amino acid sequence that is at least 95% identical to the amino acid sequence set forth in SEQ ID NO: 2, and wherein the nucleotide sequence is operably linked to a promoter;
   (b) regenerating transgenic plants from said transformed plant cells; and
   (c) selecting a transformed plant from said transgenic plants which exhibits increase in tolerance to salt stress as compared to an untransformed plant of the same species, and wherein said increase in salt tolerance is due to the expression of said polypeptide in said selected transformed plant.

2. The method of claim 1 further comprises obtaining a transformed seed from the selected transformed plant of step (c), and wherein the transformed seed comprises said recombinant nucleic acid construct and exhibits increase in tolerance to said salt stress as compared to an untransformed seed of the same species.

3. The method of claim 1, wherein said polynucleotide sequence comprises the nucleotide sequence of SEQ ID NO: 1.

4. The method of claim 1, wherein said nucleotide sequence encodes the polypeptide of SEQ ID NO: 2.

5. A method of producing a transgenic plant having an increased tolerance to drought stress, said method comprising the steps of:
   (a) transforming plant cells with a recombinant nucleic acid construct comprising a polynucleotide sequence which comprises a nucleotide sequence encoding an amino acid sequence that is at least 95% identical to the amino acid sequence set forth in SEQ ID NO: 2, and wherein the nucleotide sequence is operably linked to a promoter;
   (b) regenerating transgenic plants from said transformed plant cells; and (c) selecting a transformed plant from said transgenic plants which exhibits increase in tolerance to drought stress as compared to an untransformed plant of the same species, and wherein said increase in drought tolerance is due to the expression of said polypeptide in said selected transformed plant.

6. The method of claim 5 further comprises obtaining a transformed seed from the selected transformed plant of step (c), and wherein the transformed seed comprises said recombinant nucleic acid construct and exhibits increase in tolerance to said drought stress as compared to an untransformed seed of the same species.

7. The method of claim 5, wherein said polynucleotide sequence comprises the nucleotide sequence of SEQ ID NO: 1.

8. The method of claim 5, wherein said nucleotide sequence encodes the polypeptide of SEQ ID NO: 2.

\* \* \* \* \*